United States Patent [19]

Bøgesø

[11] 4,443,448

[45] Apr. 17, 1984

[54] INDANE DERIVATIVES, PHARMACEUTICAL COMPOSITIONS THEREOF AND METHOD OF PREPARATION

[75] Inventor: Klaus P. Bøgesø, Lyngby, Denmark

[73] Assignee: Kefalas A/S, Copenhagen-Valby, Denmark

[21] Appl. No.: 238,442

[22] Filed: Feb. 26, 1981

[30] Foreign Application Priority Data

Feb. 29, 1980 [GB] United Kingdom ................. 8006931

[51] Int. Cl.$^3$ ................. C07D 241/04; A61K 31/495
[52] U.S. Cl. .................................... 424/250; 544/369; 544/370; 544/398
[58] Field of Search ............... 544/392, 398, 369, 370; 424/250; 542/449

[56] References Cited

U.S. PATENT DOCUMENTS 2,916,490  12/1959  Schenck et al. ................... 544/398
2,982,783  5/1961   Schenck et al. ................... 544/398
3,637,740  1/1972   Sarges ................................ 544/398

OTHER PUBLICATIONS

Lewis, W. H., et al., Medical Botany, p. 381, John Wiley & Sons, N.Y.

Primary Examiner—Donald G. Daus
Assistant Examiner—S. A. Gibson
Attorney, Agent, or Firm—Gordon W. Hueschen

[57] ABSTRACT

The present invention relates to novel 1-piperazino-3-phenyl-indane derivatives which have pronounced psychopharmacological activity such as neuroleptic activity, analgesic activity, antidepressant activity and, at the same time, a low degree of undesired side-effects, methods for the preparation of said indane derivatives, pharmaceutical compositions containing same, and methods for the treatment of psychic disorders, such as psychoses and depressions and pain, by administering a therapeutically active amount of one of said derivatives to a living animal body, including human beings.

32 Claims, No Drawings

INDANE DERIVATIVES, PHARMACEUTICAL COMPOSITIONS THEREOF AND METHOD OF PREPARATION

The novel 1-piperazino-3-phenylindane derivatives of the present invention are represented by the following formula:

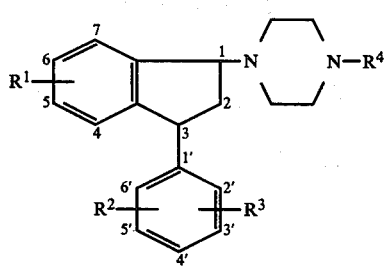

wherein $R^1$ represents hydrogen, halogen, an alkyl group having from one to four carbon atoms inclusive, an alkyloxy group having from one to four carbon atoms inclusive, an alkylmercapto group having from one to four carbon atoms inclusive, an amino or acetamino group, a cyano group, a trifluoromethyl group or an alkylsulfonyl group having from one to four carbon atoms inclusive; $R^2$ and $R^3$ are each selected from hydrogen, halogen, alkyl or trifluoromethyl, and $R^4$ represents an alkyl or alkenyl group, branched or unbranched having from one to six carbon atoms inclusive optionally substituted with one or two hydroxyl groups, a cyano group an acetamido group, a cycloalkyl group having from 3 to 6 carbon atoms in the ring, a phenyl group optionally substituted with a halogen atom a hydroxy-substituted cyclohexyl group, a group

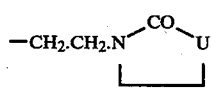

wherein $>U$ is $>O$ or $>NH$, or a group $-(CH_2)_n-CO.phenyl$ wherein "n" is an integer of from one to four inclusive, and the phenyl group may be optionally substituted with a halogen atom, any hydroxy group present in the indane of Formula I being optionally esterified with an aliphatic carboxylic acid having from two to twenty-four carbon atoms inclusive, as well as their pharmaceutically acceptable acid addition salts.

Some 1-amino-3-phenylindanes have been described as analgetic, spasmolytic and coronary dilating agents (see Adv. Drug Res. 4, 175-180 (1967)).

Recently other 1-amino-3-phenylindanes have been described in German Offenlegungsschrift No. 2 339 7 15 as having tranquilizing properties.

According to the present invention it has been found that many indanes of Formula I as well as pharmaceutically acceptable acid addition salts thereof have neuroleptic activity combined with a low degree of cataleptic activity indicating only weak unwanted extrapyrimidal side effects. Moreover, they also show analgesic activity. Others are potent dopamine uptake inhibitors indicating antidepressant activity.

The compounds of Formula I exist as geometric isomers of the cis-trans type, and it has been found in all cases that one of the isomers possesses the strongest neuroleptic and also the strongest analgesic activity. The other isomer has practically no neuroleptic activity but some analgesic activity and, moreover, in several cases has a pharmacological profile indicating antidepressant activity. For one of the compounds of Formula I, namely 1-methyl-4-(3-(4'-fluorophenyl)-6-fuoro-1-indanyl)-piperazine, it has been shown by PMR studies that the neuroleptic active isomer is the trans-isomer. Both single isomers of the indanes of Formula I as well as mixtures of isomers are within the scope of the present invention. Based upon chemical considerations such as solubility relations it is assured that the neuroleptic active isomers are of the trans-type.

Both the cis- and trans-isomers of Formula I exist as optically active isomers, and the isolation of such isomers is within the scope of the present invention. The isolation is often advantageous as the one isomer possesses practically all of the desired effects, whereas the other isomer sometimes has some unwanted side-effects.

This invention also includes pharmaceutically acceptable salts of the compounds of Formula I formed with non-toxic organic acids. Such salts are easily prepared by methods known to the art. The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, ascorbic, embonic, succinic, oxalic, bis methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic and theophylline acetic acids, as well as the 8-halotheophyllines, for exampel 8-bromo-theophylline. Exemplary of such inorganic salts are those with hydrochloric, hydrobromic, sulfuric, sulfamic, phosphoric and nitric acids. Of course, these salts may also be prepared by the classical method of double decomposition of appropriate salts, which is wellknown to the art.

The compounds of Formula I as well as the pharmaceutically acceptable acid addition salts thereof may be administered both orally and parenterally, for example in the form of tablets, capsules, powders, syrups or solutions for injection.

Of the indanes of Formula I those wherein $R^1$ is fluorine, $CF_3$, chlorine, methyl or methylmercapto in the 6-position, $R^2$ is fluorine in the 4'-position, $R^3$ is hydrogen and $R^4$ is methyl, 2-hydroxyethyl, 2,3-dihydroxypropyl, 4-hydroxybutyl, 1,3-dihydroxy-2-propyl, isopropyl or β-hydroxypropyl, are the most prominent as neuroleptics having a weak cataleptic activity and a strong analgesic activity.

The invention moreover relates to a method for the preparation of the novel indanes of Formula I, which comprises (a) reacting a compound of the following formula:

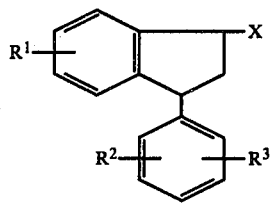

wherein $R^1$, $R^2$ and $R^3$ are as defined above and X is halogen, preferably chlorine, or $-OSO_2R$, wherein R is $CH_3$ or

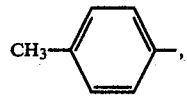

with a piperazine derivative of the formula

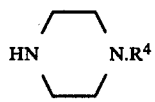

wherein $R^4$ is as defined above, or (b) reacting a compound of the following formula:

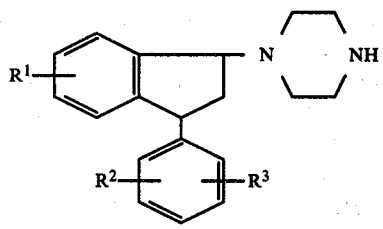

wherein $R^1$, $R^2$ and $R^3$ are as defined above, with a compound of formula $R^4.X$ wherein $R^4$ and X are defined above, or an epoxide of formula

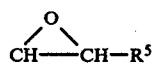

wherein $R^5$ is lower alkyl or hydroxyalkyl, or an aldehyde or ketone of formula $R^6-CO-R^7$ wherein $R^6$ is hydrogen or lower alkyl and $R^7$ is lower alkyl or alkenyl optionally substituted with phenyl or substituted phenyl using $NaCNBH_3$ as a reducing agent, or (c) reducing a compound of the following formula:

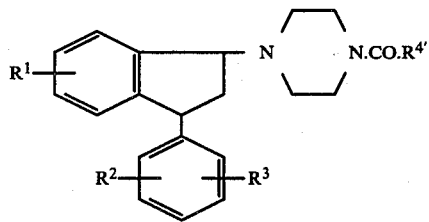

wherein $R^1$, $R^2$ and $R^3$ are as defined above, and $R^{4'}$ is an alkyl group, branched or unbranched, having from one to five carbon atoms inclusive optionally substituted with one or two hydroxyl groups which may be protected, a cycloalkyl group with from three to six carbon atoms in the ring, a phenyl group optionally substituted with a halogen atom or a hydroxy-substituted cyclohexyl group wherein the hydroxyl group may be protected, or (d) reducing a compound of the following formula:

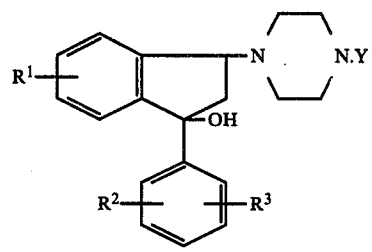

wherein $R^1$, $R^2$ and $R^3$ are as defined above, and Y is an alkyl group, branched or unbranched, having from one to six carbon atoms inclusive, optionally substituted with a cycloalkyl group having from three to six carbon atoms in the ring or a phenyl group optionally substituted with a halogen atom, or (e) reducing a compound of the following formula:

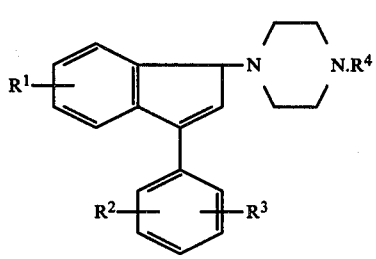

wherein $R^1$, $R^2$, $R^3$ and $R^4$ are as defined above with hydrogen in the presence of a metal catalyst, or (f) reducing a compound of formula

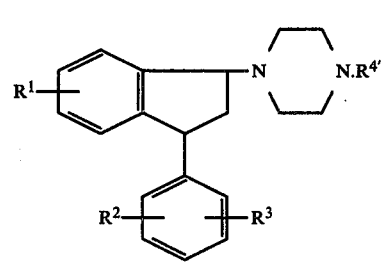

wherein $R^1$, $R^2$ and $R^3$ are as defined above, and $R^{4'}$ is a branched or unbranched alkyl or alkenyl group containing one or more ester, ketone or aldehyde groups with a suitable reducing agent to one or more hydroxy groups, whereupon the resulting compounds of Formula I is isolated, any hydroxy-group present being esterified, if desired, with a reactive derivative of an aliphatic carboxylic acid having from eight to twentyfour carbon atoms inclusive, as the free amine or an acid addition salt with a pharmaceutically acceptable acid and, if desired, separated in the individual isomers by conventional means.

Several of the intermediates of Formula II and all of the intermediates of Formulas III–VII are novel compounds and fall within the scope of the present invention.

Method (b) is preferably carried out in an inert solvent, such as acetone, an ether or an alcohol, in the presence of an alkali metal carbonate, such as potassium carbonate, or another alkaline substance, mostly at reflux temperature when $R^4.X$ is used, and in an inert solvent such as an ether or an alcohol at room temperature or higher temperatures when an epoxide is used, and in an alcohol, preferably methanol, at pH 6–8 at room temperature in the presence of 3 Å molecular sieves when $R^6$—CO—$R^7$ is used.

In method (c) the reduction may according to the invention preferably be carried out in an inert solvent, such as an ether, for example diethylether, with a reducing agent such as lithium hydride, sodium boro hydride or the like.

Apart from the reduction of the carbonyl group any hydroxy protecting group present is split off during the reduction.

The reduction according to method (d) may according to the invention preferably be carried out by means of hydroiodic acid conveniently in the presence of red phosphorous and acetic acid as a medium. Also catalytic hydrogenation in the presence of a metal catalyst may, however, according to the invention successfully be used in some cases.

In method (e) the reduction is according to the invention carried out by catalytic hydrogenation using as catalysts palladium, $PtO_2$, Raney nickel or similar catalyst.

The reaction conditions in method (f) are preferably at room temperature in the presence of an inert solvent such as ether, and a suitable reducing agent may be lithium aluminium hydride.

The intermediates of Formula II may conveniently be prepared according to the following reaction scheme:

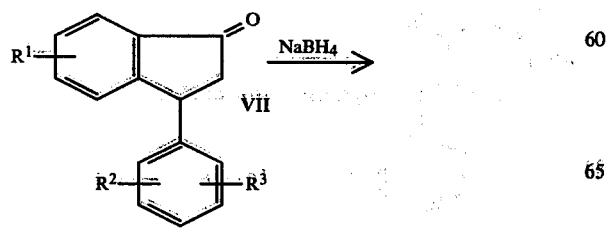

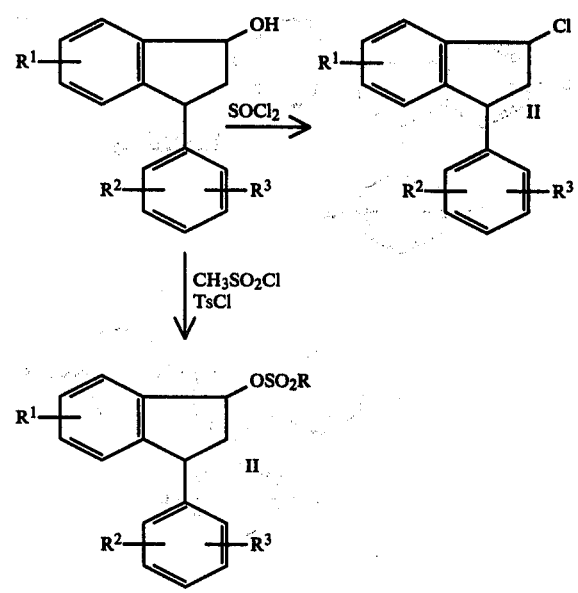

The intermediates of Formula III may conveniently be prepared according to the following scheme:

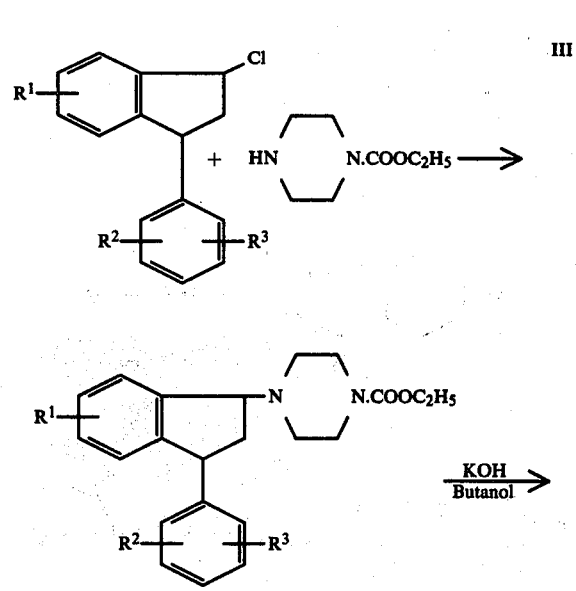

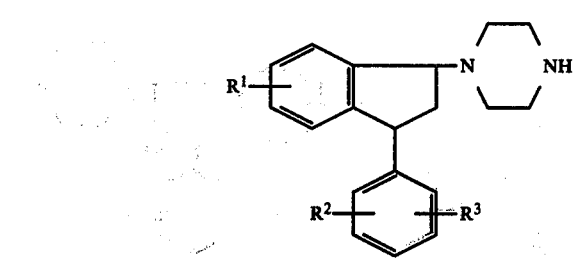

The intermediates of Formula IV may conveniently be prepared according to the following scheme:

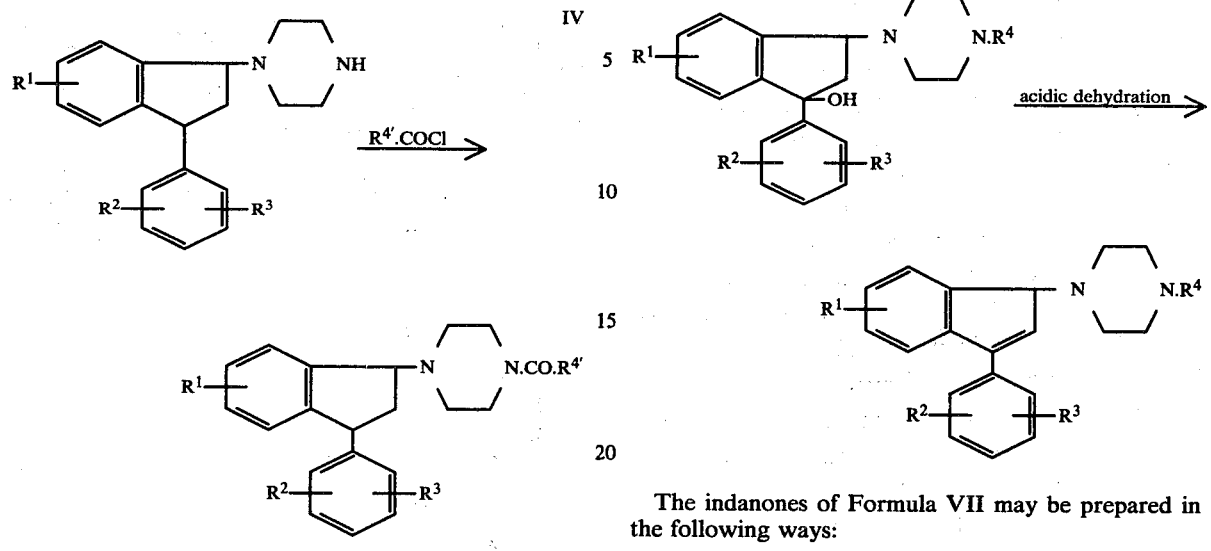
The intermediates of Formula V may conveniently be prepared according to the following scheme:
The intermediates of Formula VI may conveniently be prepared according to the following scheme:
The indanones of Formula VII may be prepared in the following ways:
Method A
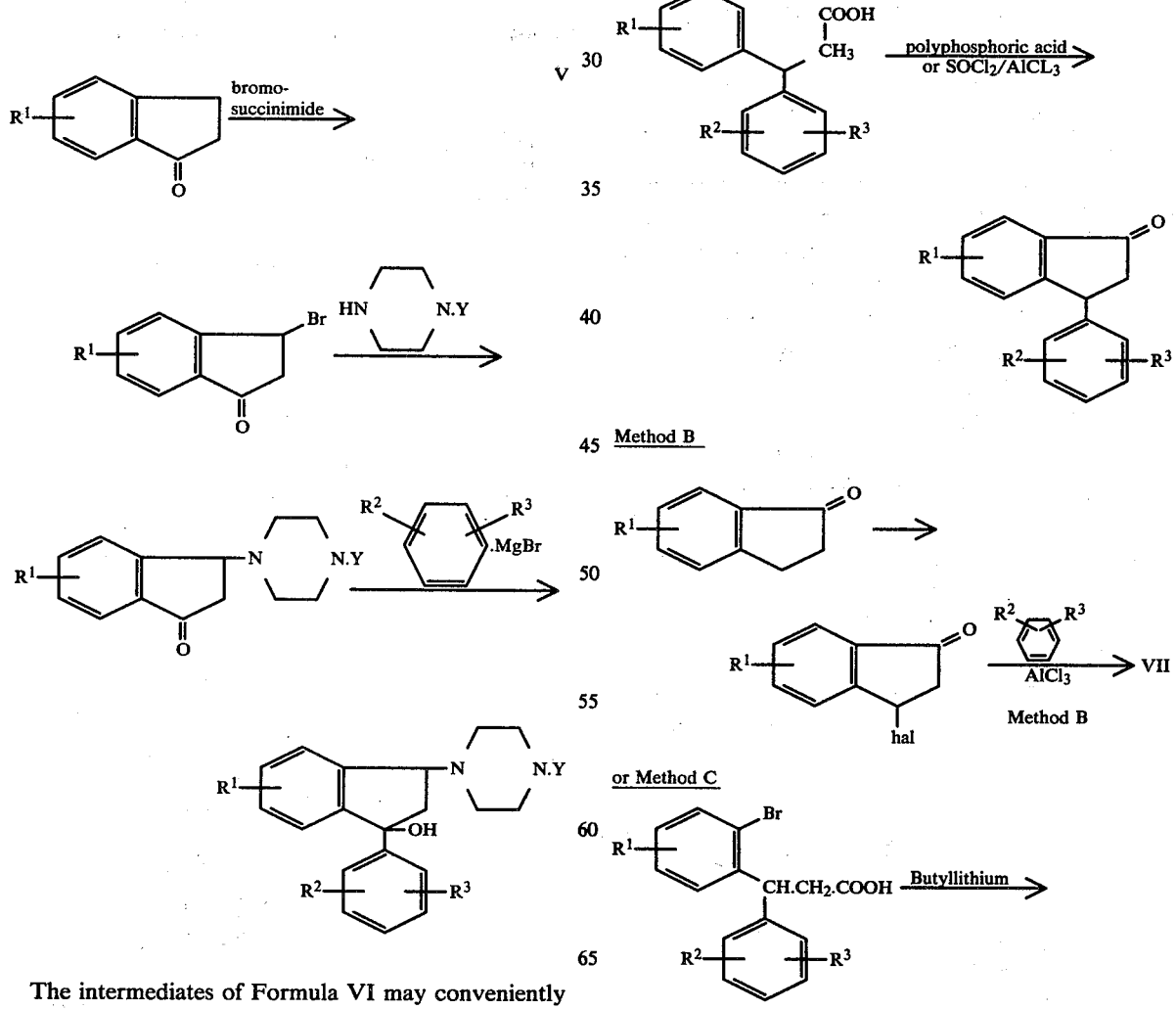
Method B
or Method C

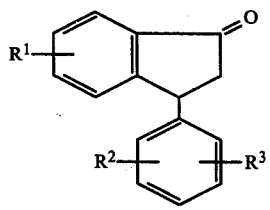

Method A was used when the ringclousure of the 3,3-diphenyl-propanoic acids could be shown predominantly to take place to one of the rings containing the most activating substituents).

Method B was used when R¹ was more deactivating than R² and R³.

Method C was used when one or more of the substituents were too sensitive to withstand the ringclosure conditions in A or B.

The structures of the indanones made by method A were proved by oxidation to the corresponding substituted 2-benzoyl benzoic acids. The identity of these acids with original samples made by unequivocal litterature methods were then shown by concordance in IR, TLC and melting point data.

The 3,3-diphenylpropionic acids used as starting materials in the firstmentioned method for preparing indanones of Formula VII may be conveniently be prepared according to a method described in Arzneimittelforschung 14, pg. 1151 (1964):

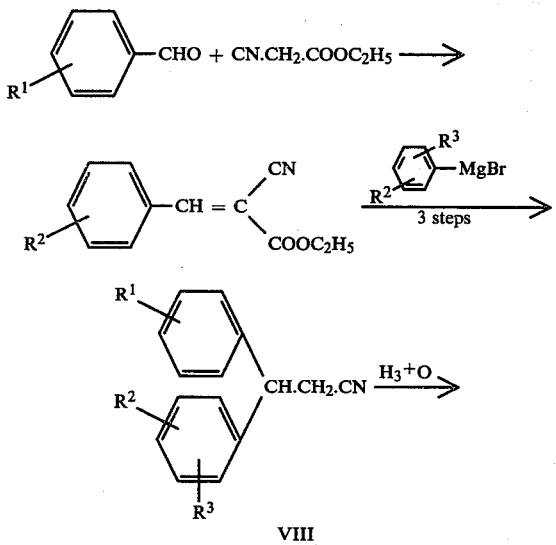

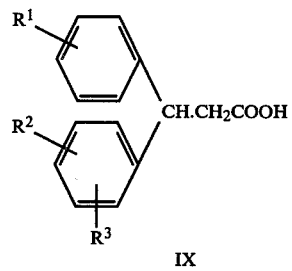

The optional esterification of any hydroxy group or groups present in the 1-piperazino-3-phenyl indane derivatives of Formula I may according to the invention conveniently be carried out with a reactive derivative of the aliphatic carboxylic acid having from eight to twentyfour carbon atoms inclusive, such as an acid chloride or anhydride. As especially suitable acids may be mentioned decanoic acid, palmitic acid and behenic acid.

The methods of the invention shall be illustrated in the following by some examples which may not be construed as limiting:

EXAMPLE 1

3-(p-fluorophenyl)-3-(p-tolyl)-propanenitrile

The substituted propanenitriles of Formula VIII may be prepared in the following way:

A solution of 860 grams of ethyl α-cyano-4-methyl-cinnamate in 1500 milliliters of hot toluene was added to a solution of 4-fluorophenyl magnesium bromide prepared from 860 grams of 4-bromofluorobenzene and 130 grams of magnesium turnings in 2500 milliliters of ether, under simultaneous distillation of the ether, until a final temperature of 80 degrees Centigrade was reached in the reaction mixture. The reaction mixture was then refluxed for 1 hour, whereupon it was hydrolysed with ice and 450 milliliters of concentrated hydrochloric acid. The mixture was then extracted with ether, washed with water, dried over anhydrous magnesium sulfate, treated with active carbon and evaporated in vacuo to give 1275 grams of crude ethyl α-cyano-3-(p-fluorophenyl)-3-(p-tolyl)-propionate.

A solution of 160 grams of sodium hydroxide in 4 liters of water was added to the ester, and the reaction mixture was warmed on steam bath until a clear solution was obtained. After treatment with active carbon 350 milliliters of concentrated hydrochloric acid were added, and the crystalline precipitate consisting of crude α-cyano-3-(p-fluorophenyl)-3-(p-tolyl)-propanoic acid was sucked off and dried.

This acid was then heated with 350 milliliters of quinoline until the temperature had risen to 180 degrees Centigrade. When the carbondioxide evolution ceased the mixture was cooled, 1 liter of toluene added and extracted with 15% hydrochloric acid until acidic reaction in the extract. The organic phase was dried over anhydrous magnesium sulfate, filtered, concentrated in vacuo and distilled to give 796 grams of 3-(p-fluorophenyl)-3-(p-tolyl)-propanenitrile boiling at 190–200 degrees Centigrade/1.5 mm Hg.

In corresponding manner were prepared other Propanenitriles of structure VIII.

TABLE 1

| R¹ | R² | R³ | BP/MP °C. |
|---|---|---|---|
| H | 4'-F | H | 58–66 |
| H | 2'-Cl | 4'-Cl | 175–180/0.4 mm |
| H | 3'-Cl | 4'-Cl | 185–200/0.5 mm |
| 2-Br | 3'-CF₃ | 4'-Cl | oil, not purified |
| 4-F | 2'-F | H | 145–165/0.3 mm |
| 4-F | 4'-F | H | 160–170/0.6 mm |
| 4-F | 3'-F | H | 160–170/0.5 mm |
| 4-F | 4'-Cl | H | oil, not purified |
| 4-Cl | 4'-Cl | H | 225–226/0.3 mm |
| 4-F | 3'-Cl | H | oil, not purified |
| 4-CH₃O | 4'-F | H | 180–195/0.5 mm |
| 4-CH₃S | 4'-F | H | 200–205/0.3 mm |
| 4-CH₃ | 4'-F | H | 190–200/1.5 mm |
| 4-(CH₃)₂CH | 4'-F | H | 160–175/0.5 mm |
| 2-Br, 4-CF₃ | H | H | oil, not purified |
| 2-Br, 4-CF₃ | 4'-F | H | oil, not purified |
| 2-Br, 4-CF₃ | 4'-Cl | H | 105–107 |
| 2-Br, 4-CF₃ | 4'-CH₃ | H | oil, not purified |
| 2-Br, 4-Cl | 4'-F | H | 190–200/0.3 mm |

TABLE 1-continued

| R$^1$ | R$^2$ | R$^3$ | BP/MP °C. |
|---|---|---|---|
| 4-Br | H | H | 82–84 |

All the compounds of Table 1 are new compounds except the compound where R$^1$ is 4-Cl, R$^2$ is 4'-Cl and R$^3$ is hydrogen, which is described in Arzneimittelforschung 14, 1151 (1964).

EXAMPLE 2

3-(p-fluorophenyl)-3-(p-tolyl)-propanoic acid

A solution of 796 grams of 3-(p-fluorophenyl)-3-(p-tolyl)-propanenitrile in a mixture of 2500 milliliters of ethanol and 800 grams of potassium hydroxide in 1000 milliliters of water was refluxed overnight. The reaction mixture was concentrated in vacuo, the residue dissolved in water and made acidic with concentrated hydrochloric acid. The crystalline acid was filtered, dissolved in 3 liters of ether, and the ether solution washed with water and dried over anhydrous magnesium sulfate. After filtration the ether solution was concentrated and hexane was added. The white crystalline acid was filtered and dried to give 827 grams of 3-(p-fluorophenyl)-3-(p-tolyl)-propanoic acid melting at 137–139 degrees Centigrade.

In corresponding manner were made the following propanoic acids of structure IX:

TABLE 2

| R$^1$ | R$^2$ | R$^3$ | MP °C. | |
|---|---|---|---|---|
| H | 4'-F | H | 111–14 | |
| H | 2'-Cl | 4'-Cl | 117–19 | new |
| H | 3'-Cl | 4'-Cl | 75–77 | new |
| 2-Br | 3'-CF$_3$ | 4'-Cl | 122–24 | new |
| 4-F | 2'-F | H | 89–91 | new |
| 4-F | 4'-F | H | 104–107 | new |
| 4-F | 3'-F | H | 103–105 | new |
| 4-F | 4'-Cl | H | 140–142 | new |
| 4-Cl | 4'-Cl | H | 193–195 | |
| 4-F | 3'-Cl | H | 95–97 | new |
| 4-CH$_3$O | 4'-F | H | 83–86 | new |
| 4-CH$_3$S | 4'-F | H | 101–103 | new |
| 4-CH$_3$ | 4'-F | H | 137–139 | new |
| 4-(CH$_3$)$_2$CH | 4'-F | H | 116–120 | new |
| 2-Br,4-CF$_3$ | H | H | 148–150 | new |
| 2-Br,4-CF$_3$ | 4'-F | H | 126–130 | new |
| 2-Br,4-CF$_3$ | 4'-Cl | H | 122–123 | new |
| 2-Br,4-CF$_3$ | 4'-CH$_3$ | H | 107–109 | new |
| 2-Br,4-Cl | 4'-F | H | 120–121 | new |
| 4-Br | H | H | 123–130 | new |
| 4-NH$_2$ | 4'-F | H | 192–195 | new |
| 4-CH$_3$CONH— | 4'-F | H | 110–115 | new |

The substances with the indication "new" are not described in the litterature.

EXAMPLE 3

3-(4'-Fluorophenyl)-6-methyl-1-indanone

Method A

300 Grams of 3-(4-fluorophenyl)-3-(p-tolyl)-propanoic acid were added while stirring to 2400 grams of polyphosphoric acid, and the resulting mixture was heated at 100 degrees Centigrade for 3½ hours. The reaction mixture was then poured unto crushed ice. The precipitated crystals were sucked off and washed with water, dissolved in ether, and the ether solution was washed with 10% aqueous sodium carbonate and water. The ether solution was then concentrated in vacuo, the residue taken up in 100 milliliters of diisopropylether and n-hexane was added. The white crystals which separated out were filtered and dried to give 225 grams of 3-(4'-fluorophenyl)-6-methyl-1-indanone melting at 68–70 degrees Centigrade.

EXAMPLE 4

3-(4'-Fluorophenyl)-6-fluoro-1-indanone

Method A

A solution of 850 grams of 3,3-bis(4-fluorophenyl)-propanoic acid in 600 milliliters of thionylchloride was refluxed for two hours and then concentrated in vacuo. The crude acid chloride was taken up in 2 liters of carbondisulfide. 850 grams of aluminiumchloride were added while stirring and cooling at a temperature of 10–15 degrees Centigrade. The reaction mixture was stirred overnight at room temperature. The reaction mixture was then poured unto crushed ice, and one liter of concentrated hydrochloric acid was added. The mixture was extracted with methylene chloride, and the organic phase was extracted with water and 1 N sodium hydroxide solution. The organic phase was then dried over anhydrous magnesium sulfate, treated with active carbon and concentrated in vacuo. The residue was taken up in hot diisopropylether, an insoluble oil was separated by decanting, and the isopropylether extract was cooled. The crystals which separated out were sucked off and dried to give 670 grams of 3-(4'-fluorophenyl)-6-fluoro-1-indanone melting at 70–73 degrees Centigrade.

In corresponding manner were made the following indanones of structure VII.

TABLE 3

| R$^1$ | R$^2$ | R$^3$ | Method | BP/MP °C. |
|---|---|---|---|---|
| H | H | H | A | 73–75 |
| 6-F | H | H | B | 58–60 |
| 6-Cl | H | H | B | 84–92 |
| H | 4'-F | H | A | 112–117 |
| H | 2'-Cl | 4'-Cl | A | 129–131 |
| H | 3'-Cl | 4'-Cl | A | 112–114 |
| H | 3'-CF$_3$ | 4'-Cl | C | oil, not purified |
| 6-F | 2'-F | H | A | 74–81 |
| 6-F | 4'-F | H | A | 78–80 |
| 6-F | 4'-Cl | H | B | 78–80 |
| 5-F | 4'-F | H | A | 100–101 |
| 6-Cl | 4'-F | H | C | 93–96 |
| 6-Cl | 4'-Cl | H | A | 114–118 |
| 5-Cl | 4'-F | H | A | 84–86 |
| 6-CH$_3$O | 4'-F | H | A | 87–90 |
| 6-CH$_3$S | 4'-F | H | A | 64–66 |
| 6-CH$_3$ | 4'-F | H | A | 68–70 |
| 6(CH$_3$)$_2$CH | 4'-F | H | A | oil |
| 6-CF$_3$ | H | H | C | oil, not purified |
| 6-CF$_3$ | 4'-F | H | C | 140/0.2 mm |
| 6-CF$_3$ | 4'-Cl | H | C | oil, not purified |
| 6-CF$_3$ | 4'-CH$_3$ | H | C | oil, not purified |
| H | 4'-Br | H | A | 50–58 |
| 6-CH$_3$CONH— | 4'-F | H | A | 177–180/85–90 |
| 6-NH$_2$ | 4'-F | H | * | 135–138 |
| 6-CN | 4'-F | H | ** | 95–105 |

*These compounds were prepared from corresponding acetamino
**compound by acid hydrolysis followed by a Sandmeyer reaction.

EXAMPLE 5

3-Phenyl-6-chloro-1-indanone

Method B

To a suspension of 275 grams of 6-chloro-1-indanone (see M. Olivier and E. Marechal: Bull.Soc.Chim.Fr. 1973 (11,Pt.2)3092-99)) in 1800 milliliters of carbontetrachloride were added 300 grams of N-Bromosuccinimide and 1 gram of dibenzoylperoxide. The reaction mixture was heated while stirring and refluxing for two hours, cooled and filtered to remove the separated succinimide. The filtrate was extracted with 1 N sodium hydroxide and water, dried over anhydrous magnesium sulfate, filtered and evaporated in vacuo. The resulting oil was taken up in hot diisopropylether, n-hexane was added, the solution was cooled, and the crystals which separated out were sucked off and dried. Upon recrystallization from 420 milliliters of n-hexane/diisopropylether (6/1) 238 grams of 3-bromo-6-chloro-1-indanone melting at 62–64 degrees Centigrade were obtained.

In a corresponding manner was made 3-bromo-6-fluoro-1-indanone melting at 62–64 degrees Centigrade, and 3-bromo-5-fluoro-1-indanone melting at 44–47 degrees Centigrade. To a solution of 113 grams of 3-bromo-6-chloro-1-indanone in 1400 milliliters of dry benzene were added over 10 minutes 230 grams of aluminiumchloride in portions. The reaction mixture was then refluxed for 3 hours, cooled and treated with crushed ice and concentrated hydrochloric acid. The organic phase was separated and extracted with 1 N sodium hydroxide and water, dried over anhydrous magnesium sulfate, treated with active carbon and concentrated in vacuo. The residue was taken up to 450 milliliters of hot n-hexane, cooled and filtered to give 96 grams of 3-phenyl-6-chloro-1-indanone melting at 84–92 degrees Centigrade.

In a corresponding manner were made 3-phenyl-6-fluoro-1-indanone melting at 58–60 degrees Centigrade and 3-(4'-chlorophenyl)-6-fluoroindanone melting at 78–80 degrees Centigrade.

EXAMPLE 6

3-(4'-fluorophenyl)-6-trifluoromethyl-1-indanone

Method C

To a solution of 40 grams of 3-(2-bromo-4-trifluoromethylphenyl)-3-(4'-fluorophenyl)-propanoic acid in 750 milliliters of dry diethylether were added dropwise 90 milliliters of butyllithium (20% in hexane). The temperature was kept between −2 and −5 degrees Centigrade, and the addition time was about 10 minutes. The reaction mixture was stirred at zero degrees Centigrade for 1½ hours; and then 400 milliliters of 2 N hydrochloric acid were added. The orgranic phase was separated and extracted twice with a 10% solution of sodium carbonate in water, then washed with water and dried over anhydrous potassium carbonate. After filtration and evaporation there was obtained 23 grams of crude 3-(4'-fluorophenyl)-6-trifluoromethyl-1-indanone. The oil was distilled in vacuo, and there was obtained 17 grams (57%) of pure 3-(4'-fluorophenyl)-6-trifluoromethyl-1-indanone boiling at 140 degrees Centigrade /0.2 mmHg.

EXAMPLE 7

3-(4'-Fluorophenyl)-6-methyl-1-indanol

A solution of 225 grams of 3-(4'-fluorophenyl)-6-methyl-1-indanone in 2.3 liters of methanol was treated with 90 grams of sodium borohydride while cooling and stirring and keeping the temperature below 20 degrees Centigrade.

The reaction mixture was then stirred in room temperature for 3 hours. After concentrating in vacuo the residue was treated with water, extracted with tolune, dried over anhydrous magnesium sulfate, filtered and evaporated in vacuo. N-hexane was added to the residue, and the crystalline precipitate was sucked off and dried to yield 208 grams of cis-trans 3-(4'-fluorophenyl)-6-methyl-1-indanol as shining white needles melting at 122–127 degrees Centigrade.

In a corresponding manner were made the following 3-phenylindanols:

TABLE 4

| R¹ | R² | R³ | MP °C. |
|---|---|---|---|
| H | H | H | 77–79 |
| 6-F | H | H | 94–99 |
| 6-Cl | H | H | 95–97 |
| H | 4'-F | H | 68–72 |
| H | 2'-Cl | 4'-Cl | oil, not purified |
| H | 3'-Cl | 4'-Cl | 55–58 |
| H | 3'-CF₃ | 4'-Cl | oil, not purified |
| 6-F | 2'-F | H | 83–85 |
| 6-F | 4'-F | H | 64–67 |
| 6-F | 4'-Cl | H | oil |
| 5-F | 4'-F | H | oil |
| 6-Cl | 4'-F | H | 136–138 |
| 6-Cl | 4'-Cl | H | 108–115 |
| 5-Cl | 4'-F | H | oil |
| 6-CH₃O | 4'-F | H | 95–97 |
| 6-CH₃S | 4'-F | H | 97–99 |
| 6-CH₃ | 4'-F | H | 122–127 |
| 6-(CH₃)₂CH | 4'-F | H | 101–104 |
| 6-CF₃ | H | H | oil, not purified |
| 6-CF₃ | 4'-F | H | 78–80 |
| 6-CF₃ | 4'-Cl | H | 104–106 |
| 6-CF₃ | 4'-CH₃ | H | 78–79 |
| H | 4'-Br | H | 100–102 |
| CH₃CO NH | 4'-F | H | 178–180 |
| 6-CN | 4'-F | H | oil, not purified |

All the indanols of Table 4—except the first one—are new compounds and fall within the scope of the present invention. They are in the form of a mixture of geometric isomers.

EXAMPLE 8

1-Methyl-4-(3-(4'-fluorophenyl)-6-fluoro-1-indanyl)piperazine, its isomers and dihydrochlorides.

Method (a)

The starting material, 1-chloro-3-(4'-fluorophenyl)-6-fluoroindane, was made in the following way:

A solution of 52 grams of 3-(4'-fluorophenyl)-6-fluoro-1-indanol in 250 milliliters of dry toluene was cooled in ice water, and a solution of 21 milliliters of thionylchloride in 21 milliliters of toluene was added dropwise keeping the reaction temperature below 10 degrees Centigrade. The reaction mixture was stirred at room temperature for 30 minutes and then slowly heated to 60 degrees Centigrade in a water-bath and kept at this temperature for one hour. The reaction mixture was then treated with ice-water, extracted with an aqueous sodium carbonate solution and dried over anhydrous magnesium sulfate. After filtration and evaporation in vacuo there was obtained 55 grams of crude 1-chloro-3-(4'-fluorophenyl)-6-fluoroindane, which was used in the next step without further purification.

A mixture of 55 grams of 1-chloro-3-(4'-fluorophenyl)-6-fluoroindane and 110 milliliters of N-methylpiperazine was heated to a temperature of 95 degrees Centigrade overnight. Crushed ice was added, and the precipitate was extracted with ether. The ether extract was washed with water and then extracted with dilute acetic acid. The acid extract was made basic with 10 N sodium hydroxide and extracted with ether. The ether extract was washed with water, dried over anhydrous potassium carbonate, treated with active carbon and evaporated in vacuo.

Yield: 60 Grams of crude product as an oil.

The oil was treated with water (200 milliliters) and concentrated hydrochloric acid to pH 3 and left overnight in the refrigerator. The dihydrochloride, which separated out, was sucked off and dried to give 7.7 grams of cis-1-methyl-4-(3-(4'-fluorophenyl)-6-fluoro-1-indanyl)piperazine, dihydrochloride in the form of monohydrate, which melted at 261–267 degrees Centigrade, and which still contained about 4% of the trans-isomer.

Melting point of the base in the form of the monohydrate: 79–81 degrees Centigrade. (Lu 13-163).

The mother liquor was made alkaline with 10 N sodium hydroxide, extracted with ether, dried over anhydrous potassium carbonate and evaporated in vacuo. The resulting oil was taken up in acetone and made acid with a saturated solution of hydrogen chloride in ether. The dihydrochloride, which precipitated out, was recrystallized twice from methanolmethylisobutylketone (1:1) to yield 16 grams of trans-1-methyl-4-(3-(4'-fluorophenyl)-6-fluoro-1-indanyl)piperazine dihydrochloride as white crystals melting at 240–243 degrees Centigrade. (Lu 13-092).

The content of cis-isomer was less than 5% as estimated by thinlayer cromatography.

In a manner corresponding to Method (a) were made the following indane derivatives of Formula I, which will be seen from Table 5.

Where both isomers were isolated, isomer I was the isomer with the lowest $R_f$, when eluted on silicagel plates using toluene-acetone-isopropylalcohol NH$_3$ 40:60:2:2 as an eluent, and also the one with the highest neurcleptic activity.

The purity of the isomers is given in percent.

TABLE 5

| Code Number | R$^1$ | R$^2$ | R$^3$ | R$^4$ | isomer % | MP °C. | |
|---|---|---|---|---|---|---|---|
| Lu 17-091 | H | H | H | CH$_3$ | I 90 | 253–255 | dihydrochloride, hydrate |
| Lu 17-090 | H | H | H | CH$_3$ | II 90 | 261–263 | dihydrochloride |
| Lu 17-061 | H | H | H | CH$_2$CH$_2$OH | I > 95 | 256–258 | dihydrochloride |
| Lu 17-060 | H | H | H | CH$_2$CH$_2$OH | II 100 | 91–93 | base |
| Lu 17-087 | H | 4'-F | H | CH$_3$ | mixture 70:30 | 258–262 | dihydrochloride |
| Lu 17-123 | H | 4'-F | H | CH$_2$CH$_2$OH | I 97 | 92–95 | base |
| Lu 17-124 | H | 4'-F | H | CH$_2$CH$_2$OH | II 95 | 112–116 | base |
| Lu 14-067 | 6-F | H | H | CH$_3$ | I 100 | 249–251 | dihydrochloride |
| Lu 14-063 | 6-Cl | H | H | CH$_3$ | I 100 | 232–242 | dihydrochloride, dihydrate |
| Lu 14-064 | 6-Cl | H | H | CH$_3$ | II 100 | 259–262 | dihydrochloride |
| Lu 18-089 | 6-CF$_3$ | H | H | —CH$_2$CH$_2$OH | I 100 | 250–253 | dihydrochloride, hydrate |
| Lu 18-090 | 6-CF$_3$ | H | H | —CH$_2$CH$_2$OH | II 100 | 232–235 | dihydrochloride, hydrate |
| Lu 17-110 | H | 3'-Cl | 4'-Cl | CH$_3$ | I 95 | 251–255 | dihydrochloride |
| Lu 17-109 | H | 3'-Cl | 4'-Cl | CH$_3$ | II 97 | 257–261 | dihydrochloride, hydrate |
| Lu 17-133 | H | 3'-Cl | 4'-Cl | CH$_2$CH$_2$OH | I > 90 | 248–253 | dihydrochloride |
| Lu 17-132 | H | 3'-Cl | 4'-Cl | CH$_2$CH$_2$OH | II 100 | 254–259 | dihydrochloride |
| Lu 18-081 | H | 3'-Cl | 4'-Cl | CH$_2$CH$_2$CH$_2$OH | I 100 | 93–94 | base |
| Lu 18-082 | H | 3'-Cl | 4'-Cl | CH$_2$CH$_2$CH$_2$OH | II > 90 | 269–272 | dihydrochloride |
| Lu 18-121 | H | 3'-Cl | 4'-Cl | —(CH$_2$)$_4$—OH | I 93 | 240–242 | dihydrochloride |
| Lu 18-120 | H | 3'-Cl | 4'-Cl | —(CH$_2$)$_4$—OH | II 98 | 244–246 | dihydrochloride |
| 18-129 | H | 3'-Cl | 4'Cl | CH$_2$CH OH CH$_2$OH | I 94 | 241–244 | dihydrochloride |
| 18-128 | H | 3'-Cl | 4'-Cl | CH$_2$CH OH CH$_2$OH | II 97 | 246–257 | dihydrochloride |
| 18-151 | H | 2'-Cl | 4'-Cl | CH$_3$ | I > 98 | 269–271 | dihydrochloride |
| 18-152 | H | 2'-Cl | 4'-Cl | CH$_3$ | II 98 | 256–258 | dihydrochloride, hydrate |
| 18-126 | H | 2'-Cl | 4'-Cl | CH$_2$CH$_2$OH | I 90 | 260–263 | dihydrochloride |
| 18-127 | H | 2'-Cl | 4'-Cl | CH$_2$CH$_2$OH | II 90 | 255–257 | dihydrochloride |
| 18-132 | H | 2'-Cl | 4'-Cl | CH$_2$CH$_2$CH$_2$OH | I > 95 | 270–272 | dihydrochloride |
| 18-133 | H | 2'-Cl | 4'-Cl | CH$_2$CH$_2$CH$_2$OH | II > 96 | 123–125 | base |
| 18-098 | H | 3'-CF$_3$ | 4'-Cl | CH$_2$CH$_2$OH | I 90 | 262–264 | dihydrochloride |
| 13-117 | 6-F | 4'-F | H | CH$_2$CH$_2$OH | I 100 | 72–74 | base |
| 17-030 | 6-F | 4'-F | H | CH$_2$CH$_2$OH | II 100 | 133–135 | base |
| 14-036 | 6-F | 4'-F | H | —(CH$_2$)$_3$OH | I 90 | 246–249 | dihydrochloride |
| 14-048 | 6-F | 4'-F | H | —(CH$_2$)$_3$OH | II 100 | 272–274 | dihydrochloride |
| 18-080 | 6-F | 4'-F | H | —(CH$_2$)$_4$OH | I 100 | 230–232 | dihydrochloride |
| 18-165 | 6-F | 4'-F | H | —(CH$_2$)$_4$OH | II 94 | 246–248 | dihydrochloride |
| 17-066 | 6-F | 4'-F | H | CH$_2$CH OH CH$_2$OH | I 90 | 181–183 | oxalate |
| 17-079 | 6-F | 4'-F | H | CH$_2$CH OH CH$_2$OH | II 90 | 114–117 | base |
| 17-071 | 5-F | 4'-F | H | CH$_3$ | mixture 1:1 | 273–275 | dihydrochloride |
| 17-075 | 5-F | 4'-F | H | —CH$_2$CH$_2$OH | I 90 | 274–276 | dihydrochloride |
| Lu 17-074 | 5-F | 4'-F | H | —CH$_2$CH$_2$OH | II 90 | 278–280 | dichloride |
| Lu 17-072 | 5-F | 4'-F | H | —(CH$_2$)$_3$—OH | mixture 70:50 | 270–272 | dihydrochloride |
| Lu 17-121 | 6-Cl | 4'-F | H | CH$_3$ | I 90 | 236–238 | dihydrochloride |
| Lu 14-069 | 6-Cl | 4'-F | H | CH$_3$ | II 90 | 238–242 | dihydrochloride |
| Lu 14-068 | 6-Cl | 4'-F | H | CH$_2$CH$_2$OH | I 95 | 244–247 | dihydrochloride |
| Lu 17-120 | 6-Cl | 4'-F | H | CH$_2$CH$_2$OH | II 90 | 243–246 | dihydrochloride |
| Lu 17-127 | 6-Cl | 4'-F | H | —(CH$_2$)$_3$—OH | I 96 | 246–249 | dihydrochloride, hydrate |
| Lu 17-113 | 5-Cl | 4'-F | H | CH$_3$ | I > 95 | 157–159 | base |
| Lu 17-114 | 5-Cl | 4'-F | H | CH$_3$ | II > 95 | 276–278 | dihydrochloride |
| Lu 17-116 | 5-Cl | 4'-F | H | CH$_2$CH$_2$OH | I 90 | 267–270 | dihydrochloride |
| Lu 17-115 | 5-Cl | 4'-F | H | CH$_2$CH$_2$OH | II 92 | 278–280 | dihydrochloride |
| Lu 17-125 | 6-Cl | 4'-Cl | H | CH$_3$ | I 85 | 238–240 | dihydrochloride monohydrate |
| Lu 17-126 | 6-Cl | 4'-Cl | H | CH$_3$ | II 99 | 80–85 | base |
| Lu 17-082 | 6-Cl | 4'-Cl | H | CH$_2$CH$_2$OH | I > 98 | 246–251 | dihydrochloride |
| Lu 17-083 | 6-Cl | 4'-Cl | H | CH$_2$CH$_2$OH | II > 98 | 252–271 | dihydrochloride monohydrate |

TABLE 5-continued

| Code Number | R¹ | R² | R³ | R⁴ | isomer % | MP °C. | |
|---|---|---|---|---|---|---|---|
| Lu 17-048 | 6-CH₃ | 4'-F | H | CH₃ | I > 97 | 246-250 | dihydrochloride |
| Lu 17-047 | 6-CH₃ | 4'-F | H | CH₃ | II 100 | 257-261 | dihydrochloride hydrate |
| Lu 17-050 | 6-CH₃ | 4'-F | H | CH₂CH₂OH | I > 94 | 170-174 | dihydrochloride hydrate |
| Lu 17-049 | 6-CH₃ | 4'-F | H | CH₂CH₂OH | II 100 | 242-244 | dihydrochloride |
| Lu 17-055 | 6-CH₃S | 4'-F | H | CH₃ | I > 95 | 235-238 | dihydrochloride |
| 17-056 | 6-CH₃S | 4'-F | H | CH₃ | II > 90 | 200-202 | dihydrochloride, hydrate |
| 17-053 | 6-CH₃S | 4'-F | H | CH₂CH₂OH | I > 90 | 230-232 | dihydrochloride |
| 17-054 | 6-CH₃S | 4'-F | H | CH₂CH₂OH | II > 90 | 158-160 | dihydrochloride, hydrate |
| 17-068 | 6-CH₃S | 4'-F | H | (CH₂)₃OH | I > 95 | 254-256 | dihydrochloride |
| 17-070 | 6-CH₃S | 4'-F | H | (CH₂)₃OH | II > 95 | 135-137 | base |
| 18-040 | 6-CH₃SO₂— | 4'-F | H | CH₃ | I 94 | 271-273 | dihydrochloride |
| 18-041 | 6-CH₃SO₂ | 4'-F | H | CH₂CH₂OH | I 100 | 265-270 | dihydrochloride |
| 18-021 | 6-(CH₃)₂CH | 4'-F | H | CH₃ | mixture 3:1 | 241-245 | dihydrochloride |
| 18-020 | 6-(CH₃)₂CH | 4'-F | H | CH₂CH₂OH | I 90 | 243-245 | dihydrochloride |
| 18-019 | 6-(CH₃)₂CH | 4'-F | H | CH₂CH₂OH | II 100 | 75-80 | base, hydrate |
| 18-014 | 6-F | 4'-Cl | H | CH₂CH₂OH | mixture 7:3 | 261-263 | dihydrochloride |
| 18-023 | 6-CF₃ | 4'-F | H | CH₃ | I > 98 | 236-239 | dihydrochloride |
| 18-044 | 6-CF₃ | 4'-F | H | CH₃ | II > 97 | 227-230 | dihydrochloride, hemihydrate |
| 18-050 | 6-CF₃ | 4'-F | H | CH(CH₃)₂ | I 100 | 126-127 | base |
| 18-051 | 6-CF₃ | 4'-F | H | CH(CH₃)₂ | II > 90 | 252-253 | hydrochloride |
| 18-012 | 6-CF₃ | 4'-F | H | CH₂CH₂OH | I > 99 | 84-85 | base |
| 18-043 | 6-CF₃ | 4'-F | H | CH₂CH₂OH | II > 97 | 186-189 | dihydrochloride |
| 18-048 | 6-CF₃ | 4'-F | H | (CH₂)₃OH | I 100 | 262-265 | dihydrochloride |
| 18-049 | 6-CF₃ | 4'-F | H | (CH₂)₃OH | II > 94 | 253-256 | dihydrochloride |
| 18-182 | 6-CF₃ | 4'-F | H | (CH₂)₄OH | I 97 | 245-247 | dihydrochloride |
| 18-183 | 6-CF₃ | 4'-F | H | (CH₂)₄—OH | II > 99 | 198-200 | dihydrochloride |
| 18-063 | 6-CF₃ | 4'-F | H | CH₂CH OH CH₂OH | I > 94 | 266-268 | dihydrochloride |
| 18-185 | 6-CF₃ | 4'-F | H | —CH(CH₂OH)(CH₂OH) | I > 99 | 152-154 | base |
| 18-074 | 6-CF₃ | 4'-Cl | H | CH₂CH₂OH | I ≧ 90 | 235-240 | dihydrochloride |
| 18-075 | 6-CF₃ | 4'-Cl | H | CH₂CH₂OH | II > 96 | 185-187 | dihydrochloride |
| 18-096 | 6-CF₃ | 4'CH₃ | H | CH₂CH₂OH | I 90 | 246-248 | dihydrochloride, hydrate |
| 18-097 | 6-CF₃ | 4'-CH₃ | H | CH₂CH₂OH | II 100 | 256-258 | dihydrochloride, hydrate |
| 18-005 | 6-CH₃O | 4'-F | H | CH₂CH₂OH | I 98 | 241-246 | dihydrochloride, hydrate |
| 18-006 | 6-CH₃O | 4'-F | H | CH₂CH₂OH | II 98 | 221-224 | dihydrochloride |
| 98/19 B | H | 4'-Br | H | —CH₂CH₂OH | I > 95 | 258-262 | dihydrochloride |
| 98/19 C | H | 4'-Br | H | CH₂CH₂OH | II > 95 | 265-272 | dihydrochloride |
| 88/289 | 6-F | 2'-F | H | CH₂CH₂OH | I > 95 | 243-245 | dihydrochloride, hydrate |
| 95/167 I | 6-CH₃CO NH | 4'-F | H | —CH₂CH₂OH | I > 95 | 140-145 | base |
| 95/167 II | 6-CH₃CO NH | 4'-F | H | —CH₂CH₂OH | II > 95 | 172-177 | base |
| 95/179 I | 6-NH₂ | 4'-F | H | —CH₂CH₂OH | I > 99 | 282-284 | trihydrochloride |
| 95/176 | 6-CN | 4'-F | H | —CH₂CH₂OH | I 98 | 255-257 | dihydrochloride |

EXAMPLE 9a

1-Isopropyl-4-(3-(4'-fluorophenyl)-6-fluoro-1-indanyl)-piperazine, mixture and isomers and dihydrochlorides

Method b1

The starting material, 1-(3-(4'-fluorophenyl)-6-fluoro-1-indanyl)piperazine, was prepared in the following way:

A mixture of 200 grams of crude 1-chloro-3-(4'-fluorophenyl)-6-fluoroindane, 200 grams of 1-ethoxycarbonylpiperazine and 140 grams of potassium carbonate in 1 liter of methylethyl ketone was refluxed overnight. After filtration, extraction with water and concentration in vacuo the residue was taken up in ether and purified by extraction with 1.5 N methanesulfonic acid. The base was liberated with 10 N sodiumhydroxide, extracted with ether and dried over anhydrous potassium carbonate. After filtration and concentraction in vacuo 200 grams of 1-ethoxycarbonyl-4-(3-(4'-fluorophenyl)-6-fluoro-1-indanyl)piperazine were obtained.

The crude product was taken up in 1 liter of n-butanol, and a solution of 200 grams of potassium hydroxide in 200 milliliters of water was added, whereupon the mixture was refluxed overnight. The reaction mixture was concentrated in vacuo, the residue treated with ether and extracted with water. The base was then purified by extraction with dilute hydrochloric acid, the base liberated with 10 N sodium hydroxide and extracted with ether. After treatment with active carbon and evaporation in vacuo 1-(3-(4'-fluorophenyl)-6-fluoro-1-indanyl)piperazine was obtained as a thick, red oil which upon standing became semi-crystalline. Yield: 140 grams.

A mixture of 35 grams of 1-(3-(4'-fluorophenyl)-6-fluoro-1-indanyl)piperazine, 13 grams of isopropylbromide and 15 grams of potassium carbonate in 200 milliliters of acetone was refluxed for 65 hours. After filtration and concentration in vacuo the residue was taken up in ether, extracted with dilute hydrochloric acid, liberated from the acid solution with 10 N sodium hydroxide, extracted with ether and the ether solution dried over anhydrous potassium carbonate.

After filtration and concentration in vacuo the base was taken up in acetone and treated with a saturated solution of hydrogen chloride in ether. The resulting dihydrochloride was recrystallized from methanol to give 5 grams of 1-isopropyl-4-(3-(4'-fluorophenyl)-6-fluoro-1-indanyl) piperazine, dihydrochloride—melting at 273-276 degrees Centigrade—called isomer II (Lu 17-043).

The other isomer was isolated from the mother liquor as the base, which was then converted to the dioxalate with oxalic acid in acetone and then recrystallized from methanol to give 6 grams of the dioxalate of isomer I (neuroleptical active isomer)—melting at 213-215 degrees Centigrade (Lu 17-062).

It contained 5-10% of isomer II.

EXAMPLE 9b 1-(2-hydroxy-1-propyl)-4-(3-(4'-fluorophenyl)-6-fluoro-1-indanyl)piperazine, mixture, and isomers, and dihydrochlorides The starting material, 1-(3-(4'-fluorophenyl)-6-fluoro-1-indanyl)piperazine, was prepared as described in Example 9a.

A mixture of 32 grams of 1-(3-(4'-fluorophenyl)-6-fluoro-1-indanyl)piperazine and 7 grams of 1,2-epoxypropane in 100 milliliters of methanol was left at room temperature overnight. The solution was filtered with charcoal and evaporated in vacuo. The resulting oil was taken up in 300 milliliters of acetone and made acidous with a saturated solution of hydrogen chloride in ether. The precipitated dihydrochloride was filtered and recrystallised twice from ethanol. There was obtained 13 grams of 1-(2-hydroxy-1-propyl)-4-(3-(4'-fluorophenyl)-6-fluoro-1-indanyl)piperazine, Isomer I as the dihydrochloride melting from 255°-258° C. Isomeric purity 95%. (Lu 17-143)

The first mother liquor from the precipitation of hydrochlorides was concentrated to the half volume whereupon isomer II crystallised. The dihydrochloride was filtered and recrystallised once from ethanol-ether to yield 1,1 grams of Isomer II melting from 262°-265° C. Isomeric purity 95%. (Lu 17-144).

EXAMPLE 9c 1-(3-Phenyl-2-propenyl)-4-(3-(4'-fluorophenyl)-6-fluoro-1-indanyl)piperazine, isomeric mixture and isomers as dihydrochlorides.

The starting material 1-(3-(4'-fluorophenyl)-6-fluoro-1-indanyl)piperazine was prepared as described in Example 9a.

To a mixture of 31 grams of 1-(3-(4'-fluorophenyl)-6-fluoro-1-indanyl)piperazine, 13.3 grams of cinnamic aldehyde and 10 grams 3 Å molecular sieves (powder) in 400 milliliters of methanol was added a saturated solution of hydrogen chloride in ether until a pH of 6 was obtained.

Then 7.8 grams of sodium cyanoborohydride were added in one portion with ice cooling, and the reaction mixture was stirred at room temperature over night.

The mixture was filtered, concentrated in vacuo, 2 N sodium hydroxide was added till strongly basic reaction, and the base was extracted with ether and purified by extraction with 2 N methane-sulfonic acid, precipitated with 10 N sodium hydroxide and reextracted with ether.

After drying ($K_2CO_3$) and evaporation 38 grams of isomeric mixture were obtained as an oil.

The isomers were separated via the oxalates as described in Example 10, and 8 grams of 1-(3-phenyl-2-propenyl)-4-(3-(4'-fluorophenyl)-6-fluoro-1-indanyl)-piperazine, Isomer I melting at 263°-265° C. were obtained as the dihydrochloride, Isomeric purity>98% (Lu 18-162), and 1 gram of Isomer II was obtained as the dihydrochloride melting at 268°-270° C., Isomeric purity>98% (Lu 18-163).

In corresponding manner were prepared the following compounds of Formula I which will appear from the following table:

TABLE 6

| Code Number | $R^1$ | $R^2$ | $R^3$ | $R^4$ | isomer % | MP °C. | |
|---|---|---|---|---|---|---|---|
| 18-088 | 6-F | 4'-F | H | —CH$_2$—C(CH$_3$)$_2$—OH | I 100 | 254-256 | dihydrochloride |
| 18-071 | 6-F | 4'-F | H | CH$_2$CH$_2$CN | I 100 | 247-249 | dihydrochloride |
| 18-095 | 6-F | 4'-F | H | CH$_2$CONH$_2$ | I 100 | 253-257 | dihydrochloride, hemihydrate |
| 18-159 | 6-F | 4'-F | H | —CH$_2$CH$_2$—C$_6$H$_5$ | I > 99 | 80-82 | base |
| 18-160 | 6-F | 4'-F | H | —CH$_2$CH$_2$—C$_6$H$_5$ | II > 99 | 75-77 | base |
| 17-039 | 6-F | 4'-F | H | 2-(2-oxazolidinon-3-yl)ethyl | I 95 | 220-223 | dihydrochloride, hydrate |
| 17-045 | 6-F | 4'-F | H | 2-(2-imidazolidinon-1-yl)ethyl | mixture 4:1 | 118-132 | base, hemihydrate |
| 17-145 | 6-F | 4'-F | H | —(CH$_2$)$_3$CO—C$_6$H$_4$—F | mixture 3:2 | 270-272 | dihydrochloride |
| 17-069 | 6-CH$_3$ | 4'-F | H | CH(CH$_3$)$_2$ | I 100 | 77-79 | base |
| 18-042 | 6-CH$_3$ | 4'-F | H | CH(CH$_3$)$_2$ | II ≧ 97 | 247-249 | dihydrochloride |
| 18-156 | 6-CH$_3$ | 4'-F | H | 2-(2-oxazolidinon-3-yl)ethyl | I > 99 | 111-112 | base |
| 17-111 | 6-CH$_3$S | 4'-F | H | CH(CH$_3$)$_2$ | I > 95 | 250-252 | dihydrochloride |

TABLE 6-continued

| Code Number | R$^1$ | R$^2$ | R$^3$ | R$^4$ | isomer % | MP °C. | |
|---|---|---|---|---|---|---|---|
| 17-112 | 6-CH$_3$S | 4'-F | H | CH(CH$_3$)$_2$ | II 95 | 229–232 | dihydrochloride |
| 17-092 | 6-CH$_3$S | 4'-F | H | 2-(2-oxazolidinon-3-yl)ethyl | mixture 7:3 | 213–215 | dihydrochloride |
| 17-129 | 6-Cl | 4'-F | H | CH(CH$_3$)$_2$ | I 95 | 260–262 | dihydrochloride, hemihydrate |
| 17-128 | 6-Cl | 4'-F | H | CH(CH$_3$)$_2$ | II 90 | 278–280 | dihydrochloride, hemihydrate |

EXAMPLE 10

1-Cyclopropylmethyl-4-(3-(4'-fluorophenyl)-6-fluoro-1-indanyl)piperazine isomeric mixture, isomers and their hydrochlorides

Method (c)

The starting material, 1-cyclopropylcarbonyl-4-(3-(4'-fluorophenyl)-6-fluoro-1-indanyl)piperazine, was prepared in the following way:

To a solution of grams of 1-(3-(4'-fluorophenyl)-6-fluoro-1-indanyl)piperazine in 200 milliliters of dry toluene were added 15 grams of cyclopropanecarbonyl chloride. The reaction mixture was stirred for 30 minutes at 70°–80° C., cooled, and the crystalline hydrochloride, which separated out, was filtered.

The hydrochloride was converted to the base with dilute sodium hydroxide solution, extracted with toluene, dried over anhydrous potassium carbonate, filtered and evaporated in vacuo to give 40 grams of 1-cyclopropylcarbonyl-4-(3-(4'-fluorophenyl)-6-fluoro-1-indanyl)piperazine as an oil.

A solution of 40 grams of 1-cyclopropylcarbonyl-4-(3-(4'-fluorophenyl)-6-fluoro-1-indanyl)piperazine in 250 milliliters of dry ether was added dropwise to a suspension of 10 grams of lithium aluminium hydride in 75 milliliters of ether. The reaction mixture was then refluxed over night and hydrolysed with water. The etherphase was decanted from the inorgranic salts which was extracted twice with ether. The combined etherphases were extracted with 2 N methanesulfonic acid, the base liberated with 10 N sodium hydroxide, and extracted with ether. The etherphase was dried over potassium carbonate, filtered and evaporated to give 38 grams of crude base.

The base was taken up in 400 milliliters of 80% methanol and made acidic with a saturated solution of oxalic acid in acetone. The oxalate was filtered and boiled with 1 liter of 80% methanol and then cooled to room temperature. The oxalate was filtered and converted to the base with dilute sodium hydroxide, extracted with ether, which was dried over anhydrous potassium carbonate, filtered and evaporated in vacuo. The base was taken up in 200 milliliters of ethanol and made acidic with a saturated solution of hydrogen chloride in ether. The dihydrochloride was filtered and dried to give 17 grams of 1-cyclopropylmethyl-4-(3-(4'-fluorophenyl)-6-fluoro-1-indanyl)piperazine as white crystals melting at 254°–256° C. Isomer>99% isomeric purity. (Lu 18-157)

The combined filtrates from the oxalates were evaporated, and the residue was converted to the base with dilute sodium hydroxide, extracted with ether and converted to the dihydrochloride as described for isomer I. There was obtained 3 grams of isomer II, isomeric purity>98%, melting at 260°–262° C. (Lu 18-158).

In corresponding manner were prepared:

TABLE 7

| Code Number | R$^1$ | R$^2$ | R$^3$ | R$^4$ | isomer % | MP °C. | |
|---|---|---|---|---|---|---|---|
| 18-169 | 6-F | 4'-F | H | C$_2$H$_5$ | I 99 | 250–252 | dihydrochloride, hemihydrate |
| 18-170 | 6-F | 4'-F | H | C$_2$H$_5$ | II 98 | 268–270 | dihydrochloride |
| 17-100 | 6-F | 4'-F | H | —CH$_2$—cyclohexyl | mixture 1:1 | 255–275 | dihydrochloride |
| 17-059 | 6-F | 4'-F | H | —CH$_2$—cyclohexyl—OH (trans) | I > 90 | 239–241 | dihydrochloride |
| 17-130 | 6-CH$_3$ | 4'-F | H | —CH$_2$—cyclopropyl | 90 | 250–252 | dihydrochloride |

EXAMPLE 11

1-Methyl-4-(3-(4'-fluorophenyl)-6-fluoro-1-indanyl)piperazine and its dihydrochloride

Method (d)

The starting material, 1-methyl-4-(3-(4'-fluorophenyl)-3-hydroxy-6-fluoro-1-indanyl)piperazine, was prepared in the following way:

A solution of 13.5 grams of 1-methylpiperazine in 30 milliliters of dry toluene was added dropwise while cooling and stirring to a solution of 14 grams of 3-bromo-5-fluoroindanone in 180 milliliters of dry toluene keeping the temperature below 10 degrees Centigrade. The reaction mixture was then stirred for one hour at 5 degrees Centigrade and half an hour at room temperature. After filtration from methylpiperazine hydrobromide the filtrate was washed with water, dried over anhydrous potassium carbonate, treated with active carbon and evaporated in vacuo to give 12.3 grams of a brown oil, which crystallized from isopropylether-petroleum ether (1:1) to give 10 grams of pure 1-methyl- 4-(5-fluoro-1-oxo-indan-3-yl)piperazine, melting at 102–103 degrees Centigrade.

To a solution of 4-fluorophenyl magnesium bromide in ether, prepared from 21 grams of 4-bromofluorobenzene and 3.2 grams of magnesium turnings in 100 milliliters of ether, were added dropwise 23 grams of 1-methyl-4-(5-fluoro-1-oxo-indan-3-yl) piperazine in 130 milliliters of tetrahydrofuran. The reaction mixture was refluxed for 2 hours and then hydrolyzed with ice and a saturated ammonium chloride solution. The base was extracted with ether, washed with water and dried over anhydrous potassium carbonate. After treatment with active carbon and evaporation in vacuo 28.7 grams of crystalline product which after recrystallization from isopropylether yielded 22 grams of pure 1-methyl-4-(3-(4'-fluorophenyl)-3-hydroxy-6-fluoro-1-indanyl)piperazine melting at 136–139 degrees Centigrade were obtained.

A mixture of 10 grams of 1-methyl-4-(3-(4'-fluorophenyl)-3-hydroxy-6-fluoro-1-indanyl-piperazine, 80 milliliters of glacial acetic acid, 50 milliliters of 57% hydroiodic acid, 6.3 grams of red phosphorous ans 3 milliliters of water was refluxed for 4 hours. After filtration the solution was made basic with concentrated aqueous ammonia and extracted with ether. The organic phase was washed with water and extracted with dilute acetic acid. The acid extract was made basic with 10 N sodium hydroxide and extracted with ether. The organic phase was dried over anhydrous potassium carbonate, filtered and evaporated in vacuo to yield 4.5 grams of the base as an oil.

The base was taken up in acetone and made acid with a saturated solution of hydrogen chloride in ether. The hydrochloride which precipitated out was sucked off and recrystallized from methanol to give 4 grams of 1-methyl-4-(3-(4'-fluorophenyl)-6-fluoro-1-indanyl)piperazine, dihydrochloride melting at 265–269 degrees Centigrade (Isomer II).

EXAMPLE 12

1-Methyl-4-(3-(4'-fluorophenyl)-6-fluoro-1-indanyl)piperazine and its cis-isomer The starting material, 1-methyl-4-(3-(4'-fluorophenyl)-6-fluoro-1-indenyl)piperazine, was prepared in the following way:

A mixture of 7 grams of 1-methyl-4-(3-(4'-fluorophenyl)-3-hydroxy-6-fluoro-1-indanyl)piperazine, 40 milliliters of concentrated hydrochloric acid and 20 milliliters of glacial acetic acid was refluxed for one hour. The reaction mixture was poured onto crushed ice, made basic with aqueous ammonia and extracted with ether. The organic phase was dried over potassium carbonate, filtered and evaporated to give 6.5 grams of a yellow oil. The oil was taken up in petroleum ether, from which was obtained on cooling 2.5 grams of pure 1-methyl-4-(3-(4'-fluorophenyl)-6-fluoro-1-indenyl)piperazine, which melted at 74–76 degrees Centigrade.

To a solution of 4 grams of 1-methyl-4-(3-(4'-fluorophenyl)-6-fluoro-1-indenyl)piperazine in 100 milliliters of ethanol were added 0.4 grams of PtO$_2$, and the resulting mixture was hydrogenated for one hour on a Parr-apparatus at room temperature and 3 atmospheres of pressure. The reaction mixture was filtered and evaporated in vacuo. The resulting oil was taken up in acetone and made acid with a saturated solution of hydrogen-chloride in ether. The resulting hydrochloride was sucked off and drived to give 4.3 grams of pure cis-1-methyl-4-(3-(4'-fluorophenyl)-6-fluoro-1-indanyl)piperazine, melting at 265–269 degrees Centigrade.

EXAMPLE 13

Method (f)

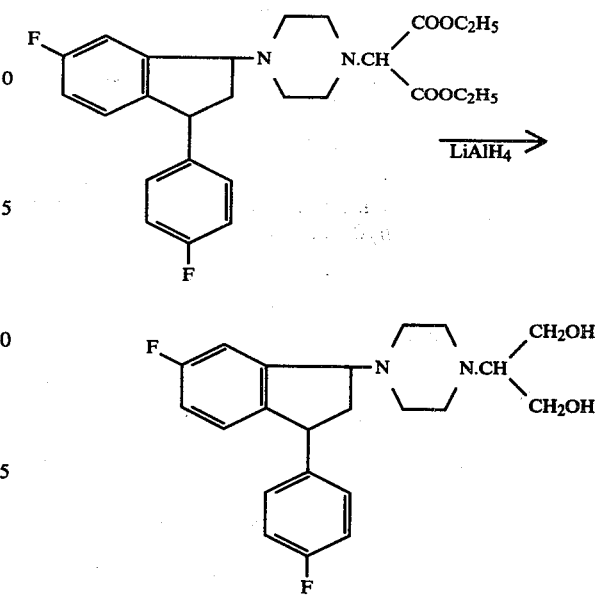

The starting material was prepared according to method (b1) from 31 grams of 1-(3-(4'-fluorophenyl)-6-fluoro-1-indanyl)-piperazine and 30 grams bromo diethylmalonate to yield 53 grams of 1-bis(ethoxycarbonyl)methyl-4-(3-(4'-fluorophenyl)-6-fluoro-1-indanyl)piperazine as an oil.

A solution of 53 grams of crude 1-bis(ethoxycarbonyl)methyl-4-(3-(4'-fluorophenyl)-6-fluoro-1-indanyl)piperazine in 200 milliliters of ether was added dropwise to 8 grams of lithium aluminium hydride in 100 milliliter ether at reflux temperature. The reaction mixture was refluxed for 2 hours and then hydrolysed with water. After filtration the base was purified by extraction from the ether phase with dilute hydrochloric acid, whereupon the base was liberated with 10 N sodium hydroxide and extracted with ether. The ether phase was dried over potassium carbonate, filtered and evaporated to give the isomeric mixture as an oil.

The isomers were separated via the oxalates as described in Example 10, and then converted to the dihydrochlorides, Yield: 6 grams of 1-(1,3-dihydroxy-2-propyl)-4-(3-(4'-fluorophenyl)-6-fluoro-1-indanyl)piperazine, dihydrochloride, melting at 245°–247° C. Isomer I 99% (Lu 18-134) and 1.6 grams Isomer II (purity 95%) melting at 250°–252° C. (Lu 18-135).

EXAMPLE 14

Decanoic acid ester of 1-(2-hydroxyethyl)-4-(3-(4'-fluorophenyl)-6-fluoro-1-indanyl)-piperazine To a solution of 8.5 grams of 1-(2-hydroxyethyl)-4-(3-(4'-fluorophenyl)-6-fluoro-1-indanyl)piperazine in 250 ml acetone was added 10 grams of decanoyl chloride, whereupon the reaction mixture was refluxed for 30 minutes. After cooling to room temperature a saturated solution of hydrogen chloride in ether was added until a pH of 3. The resulting dihydrochloride was filtered, washed with ether and dried to give 12 grams of the decanoic acid ester of Lu 13-117, melting at 221°–225° C. (Lu 17-146).

In corresponding manner were prepared:

The dihydrochloride of Lu 13-117 palmitate, 1-(2-hydroxyethyl)-4-(3-(4'-fluorophenyl)-6-fluoro-1-indanyl)piperazine, palmitate, melting at 227°–229°C. (Lu 18-018).

The base of Lu 13-117 behenate, 1-(2-hydroxyethyl)-4-(3-(4'-fluorophenyl)-6-fluoro-1-indanyl)piperazine, behenate, melting at 60°–61° C. (Lu 18-017).

The dihydrochloride of Lu 18-012 valerate, 1-(2-hydroxyethyl)-4-(3-(4'-fluorophenyl)-6-trifluoromethyl-1-indanyl)piperazine, valerate, melting at 220°–223° C. (Lu 18-131). The dihydrochloride of Lu 18-012 decanoate, 1-(2-hydroxyethyl)-4-(3-(4'-fluorophenyl)-6-trifluoromethyl-1-indanyl)piperazine, decaonate, melting at 198°–200° C. (Lu 18-184).

EXAMPLE 15

(+) and (−) 1-Methyl-4-(3-(4'-fluorophenyl)-6-fluoro-1-indanyl)piperazine, and their dihydrochlorides To a solution of 39 grams of 1-methyl-4-(3-(4'-fluorophenyl)-6-fluoro-1-indanyl)piperazine, (Lu 13-092 base, pure isomer I, racemic mixture), in 300 milliliters of ethylacetate were added 44.5 grams of (+)-O,O'-dibenzoyl-D-tartaric acid, and the mixture was warmed until a clear solution was obtained. The mixture was left in the refrigerator over night; the precipitate was filtered and recrystallised from 200 ml ethylacetate and 200 milliliters of acetone, to give 24 grams of the (+)-O,O'-dibenzoyl-D-tartaric acid salt of the (+)-isomer of Lu 13-092, melting at 145°–146° C. This salt was converted to the free base with dilute sodium hydroxide, extracted with ether, dried over magnesium sulfate and evaporated in vacuo. The resulting base was taken up in acetone which was made acidous with a saturated solution of hydrogen chloride in ether. 12 grams of (+) 1-Methyl-4-(3-(4'-fluorophenyl)-6-fluoro-1-indanyl) piperazine were obtained as the dihydrochloride, melting at 249°–251° C., $[\alpha]_D^{22} = +19.8°$ (c=5%, MeOH). (Lu 17-151)

The first mother liquor from the O,O-dibenzoyl-D-tartaric precipitation was evaporated in vacuo, and the residue was converted to the free base with dilute sodium hydroxide, extracted with ether and dried over magnesium sulfate. After filtration and evaporation the base was taken up in 150 milliliters of hot ethylacetate, whereupon 10.5 grams D-(−)-tartaric acid was added. After cooling the precipitate was filtered and dried to yield 28 grams, melting at 200°–202° C.

After recrystallisation from 500 milliliters of methanol 18.5 grams of the (−)-isomer of Lu 13-092, D-(−)-tartrate were obtained, melting at 207°–209° C. The tartrate was converted to the base, which was precipitated as the dihydrochloride in acetone as described for the (+) isomer, to give 10 grams of (−) 1-Methyl-4-(3-(4'-fluorophenyl)-6-fluoro-1-indanyl)piperazine as the dihydrochloride, melting at 252°–254° C.,$[\alpha]_D^{22} = 19.8°$ (c=5%, MeOH), (Lu 17-152). The novel indanes of Formula I were tested pharmacologically in standard and reliable animal tests.

Where the results with salts were compared with the results obtained with the free base it was found that the effect was the same as that obtained with the equivalent amount of free base.

The tests may be described as follows:

Methylphenidate antagonism (ED50 mg/kg i.p.)

Perspex observation cages without bottom and lid, consisting of 5 sections each measuring 12×25×30 cm.
White corrugated paper.
Mice, male, 18–25 g.

Dosage and procedure

The test substance is given i.p. in the doses 0, ⅛, 1/32 and 1/128 of the determined "i.p. LD50". 3×2 mice are used for each dose level. Two or 24 hours after injection of test substance, methylphenidate, 60 mg/kg, is injected s.c. After administration of methylphenidate the mice are placed in the observation cages, 2 in each cage, where they remain for exactly 1 hour. The cages were placed on corrugated paper, the corrugations facing upwards. It is examined whether the mice have been biting the corrugated paper or not. If not, the substance has had an antagonistic effect. If one or more of the control pairs have not been biting, the test has to be repeated on a new set of mice.

The result is stated in fractions: 0/3, 1/3, 2/3 and 3/3 where 0, 1, 2 and 3 are the number of pairs which have not been biting on receipt of the dose in question.

The results are calculated as the dose (ED$_{50}$), which causes antagonism in 50% of the test animals.

Amphetamine antagonism (ED$_{50}$ mg/kg i.p.)

Perspex observation cages without bottom and lid, consisting of 5 sections each measuring 12×25×30 cm.
While corrugated paper.
Rats, male, 230–270 g.

Dosage and procedure

The test substance is given p.o. in a reasonable dose based on the determined LD$_{50}$. Two or 24 hours later an intravaneous injection of amphetamine sulphate 13.6 mg/kg (10 mg/kg amphetamine base) is given, after which the rats are placed individually in the cages. The cages are placed on white corrugated paper. Five rats are used for each dose level. Observations are made after 55 minutes and 65 minutes-observation time: 1 minute. The animals are observed for stereotypy (movements of the head, compulsive gnawing). If no stereotypy is demonstrated the substance has had an antagonistic effect. If the compound has full antagonistic effect another group of rats is used at a lower dose. If the compound shows no effect a higher dose is used. The result is stated as fractions: 0/5, 1/5, 2/5, 3/5, 4/5 and 5/5, where 0, 1, 2, 3, 4 and 5 indicate the number of rats which have not shown stereotypy at the dose in question. The results are calculated as ED$_{50}$ in mg/kg.

Catalepsy wire mesh, rat, max, (ED$_{50}$ mg/kg p.o.)

A vertical wire netting (50 cm×49 cm). The meshes (openings) of the netting are square (1 cm×1 cm). The wire diameter is 2 mm.
Stop watch.
Rats, male, 180–200 g.

Dosage and procedure

The animals are labeled and used in groups of five. The test substance is administered orally (p.o) at 4 dose levels selected from the fixed dose scale.

The animals are placed in the middle of the vertical wire netting 60, 120, 180, 240, 300 and 360 minutes after administration of the test compound. The animals are considered cataleptic when they remain immobile during a period of 15 seconds.

This cataleptic reaction is designated +. If the rats are "atonic" and passively slide down the wire mesh they are considered not cataleptic. If the animals climb up and down the wire mesh they are nor cataleptic.

In both situations the designation—is used.

The results are recorded in fractions: 0/5, 1/5, 2/5, 3/5, 4/5 and 5/5, where 0, 1, 2, 3, 4 and 5 are the number of rats with designation + at the time where dose in question possessed the strongest effect within the first 6 hours.

Mouse grid shock

Mice, male, 20–23 g.

The mouse grid consists of a perspex cage with wire grid bottom and a perspex lid, on which is placed a microphone sensitive to the frequency of a mouse squeak. A stimulator with motordriven potentiometer applies a sequence of square wave impulses of continuously increasing milliamperage to the grid. Frequency of impulses 20 cycles/sec., duration 5 msec. Milliamperage is recorded on a digital amperemeter connected to the stimulator. Activation of the microphone by a mouse-squeak cuts off the current and the final milliamperage appears on the meter.

Dosage and procedure

The test substance is given i.p. in the doses ½, ¼ and ⅛ of the determined "i.v. LD50". For insoluble substances the doses ¼, ⅛ and 1/16 of the "i.p. LD50" are used. Five mice are used for each dose level. Each mouse serves as its own control.

Prior to the administration of test substance the animals are placed on the grid one at a time, and the pain threshold is determined by increasing the current intensity until the mouse squeaks. The pain threshold may be read on the milliamperemeter. Fifteen minutes and 30 minutes after administration of test substance the mice are tested again and the pain thresholds recorded. Furthermore the test substance may be tested after oral administration in doses 1/1, ½ and ¼ of the "i.v. LD50", and the pain threshold is determined before and 30 minutes after the administration. Insoluble test substances are tested orally in the doses of ½, ¼ and ⅛ of the "i.p. LD50".

Analgesic effect is present, when the pain threshold is increased over the pre-dosing value (control value). The results are stated as % increase in pain threshold calculated on the basis of the control value.

The registration can also be done as an on-line procedure. In this case the punching instruction and punching cards will be provided automatically and the results will be registered as a minimal effective dose (MED) determined after van der Waerdens X-test.

$^3$H-DA uptake in striatal synaptosomes in vitro

Rats, 180–220 g
0.32 M sucrose containing 1 mM Nialamide
Krebs-Ringer-phosphate buffer, pH 7.4 (122 mM NaCl, 4.8 mM KCl, 972 μM CaCl$_2$, 1.2 mM MgSO$_4$, 12.7 mM Na$_2$HPO$_4$, 3.0 mM NaH$_2$PO$_4$, 162 μM EDTA-Na$_2$, 1.14 mM ascorbic acid, 10.1 mM glucose, oxygenated with pure oxygen 10 min. before use)
Millipore filters (HAWPO 2500, 0.45μ)
3,4-dihydroxyphenylethylamine[ethyl-1-$^3$H(N)]=$^3$H-DA spc. act. app. 15 Ci/mmol, New England Nuclear Thomas Tissue Grinder, clearance 0.004–0.006 inch.

Procedure

Rats are killed by a blow to their head, exsanguinated and their brains removed. The brain is placed on a precooled glassplate, and the two corpura striata are dissected out and gently homogenized in 40 volumes of ice cold 0.32 M sucrose containing 1 mM of nialamide using a hand homogenizer with teflon pestle. The P$_2$-fraction (synaptosomal fraction) is obtained by centrifugation (600 g, 10 min., 25000 g, 55 min. 4° C.) and suspended in 40 volumes of a modified Krebs-Ringer-phosphate buffer, pH 7.4. To 200 μl of the synaptosomal fraction on ice are added 3700 μl modified Krebs-Ringer-phosphate buffer—containing test compounds. After a preincubation at 37° C. for 5 min. 100 μl of $^3$H-DA (final conc. 12.5 nM) are added, and the samples are incubated for 5 min. at 37° C. The incubation is terminated by filtering the samples under vacuum through Millipore filters with a wash of 5 ml buffer containing 10 μM of unlabelled DA. After solubilizing the filters in 1 ml of cellosolve the radioactivity is determined by liquid scintillation counting after the addition of 10 ml of Insta-Gel. The unspecific binding of $^3$H-DA is determined by incubating control samples on ice instead of at 37° C.

All experiments are performed in triplicate.

The mean of all control samples and ice samples are calculated. The measured cpm in the samples are plotted against drug concentration on semilogarithmic paper, and the best fitting S-shaped curve drawn. The IC50-values are determined as the concentrations, at which the uptake are 50 percent of the uptake in control samples-uptake in ice samples.

The results obtained appear from Table 8, where the effects obtained have been compared with chlorpromazine, fluphenazine and haloperidol, in so far as the neuroleptic effects are concerned, and with morfine, codeine and dextropropoxyphene when analgesic effects are concerned using the grid shock test for comparison.

TABLE 8

| Code No. | MePh antag. ED$_{50}$ 2 hr i.p. | Amphetamine antag. ED$_{50}$ p.o. | Catalep. | Ratio catalep. Amphet. | MED Grid Shock | LD$_{50}$ i.v. |
|---|---|---|---|---|---|---|
| Lu 13-092 | 4.2 | 14.8 | 81 | 5.5 | 1.3 | 80 |
| Lu 13-117 | 3 | 6 | 79 | 13 | 0.63 | 113 |
| Lu 14-036 | 1.6 | 2.3 | 3.7 | 1.6 | 5/46 | 129 |
| Lu 14-063 | 29 | >40 | >40 | | 5 | 80 |
| Lu 14-067 | >40 | | | | 5 | |
| Lu 14-068 | 1.3 | 1.6 | 1.5 | 0.9 | 0.31 | 94 |
| Lu 14-069 | 5.7 | >20 | >40 | | 5 | 65 |
| Lu 17-039 | 9.1 | 51 | >80 | | | 113 |
| Lu 17-045 | >40 | >80 | >80 | | 2.5 | |

TABLE 8-continued

| Code No. | MePh antag. ED$_{50}$ 2 hr i.p. | Amphetamine antag. ED$_{50}$ p.o. | Catalep. | Ratio catalep. Amphet. | MED Grid Shock | LD$_{50}$ i.v. |
|---|---|---|---|---|---|---|
| Lu 17-048 | 0.6 | 6.7 | 4.8 | 0.7 | 0.16 | 80 |
| Lu 17-050 | 3.4 | 9.4 | 7.7 | 0.8 | 0.63 | 80 |
| Lu 17-053 | 1.3 | 9.1 | 6.2 | | 2.5 | 68 |
| Lu 17-055 | 1.2 | 10 | 7.2 | 0.7 | 5/36 | 68 |
| Lu 17-056 | 20 | | | | 5 | |
| Lu 17-059 | 4.3 | 28 | >40 | >1.4 | 5 | 94 |
| Lu 17-061 | >40 | | | | 10 | |
| Lu 17-062 | 1.3 | 10 | 14 | 1.4 | 5 | 113 |
| Lu 17-066 | 1.6 | 18 | >160 | 8.9 | 2.5 | >160 |
| Lu 17-068 | 0.8 | 1.8 | 1.3 | 0.7 | 0.31 | 94 |
| Lu 17-069 | 0.8 | 5.6 | 6.7 | 1.2 | 0.63 | 56 |
| Lu 17-071 | >40 | | 31 | | 10 | |
| Lu 17-075 | 6.0 | >40 | >40 | | 2.5 | 80 |
| Lu 17-091 | >40 | | | | 10 | |
| Lu 17-100 | 4 | >40 | 40 | | 10 | 93 |
| Lu 17-111 | 2.3 | 7.8 | 7.1 | 0.9 | 1.3 | 69 |
| Lu 17-116 | >40 | | | | 10 | |
| Lu 17-120 | 3.2 | | >20 | | 2.5 | |
| Lu 17-121 | 2 | 10 | 3 | 0.3 | 0.63 | 68 |
| Lu 17-124 | >40 | | | | 5 | |
| Lu 17-127 | 0.4 | 0.3 | 0.5 | 1.7 | 0.31 | 80 |
| Lu 17-129 | 0.8 | 1.8 | 0.8 | 0.4 | 5 | 80 |
| Lu 17-130 | 5 | >40 | >40 | | 5 | |
| Lu 17-143 | 1.2 | 5.4 | 16.6 | 3.1 | <1.3 | 130 |
| Lu 17-145 | >40 | | | | 5 | |
| Lu 17-151 | 1.0 | 6.1 | 16.4 | 2.7 | 0.63/25 | 113 |
| Lu 17-152 | 17 | >80 | >320 | | 5 | |
| Lu 18-006 | 8.6 | 16.6 | 12 | 0.7 | 5/30 | 113 |
| Lu 18-012 | 0.03 | 0.16 | 0.3 | 2 | 0.6 | 56 |
| Lu 18-020 | 4.4 | 9.4 | 7.8 | 0.8 | 5 | 57 |
| Lu 18-023 | 1.1 | 0.2 | 0.4 | 2 | 1.25/30 | 94 |
| Lu 18-040 | 8.3 | 12 | 10 | 0.8 | >20 | 130 |
| Lu 18-041 | 10 | | | | 5 | >160 |
| Lu 18-048 | 0.12 | 0.16 | 0.07 | 0.4 | 1.3 | 57 |
| Lu 18-050 | 0.44 | 0.22 | 0.52 | 2.4 | 10 | 57 |
| Lu 18-063 | 0.4 | 0.12 | 0.38 | 3.2 | 1.25 | 57 |
| Lu 18-080 | 2.9 | 3.5 | 21.8 | 6.2 | <1.3 | 80 |
| Lu 18-089 | 2.2 | 5 | 2.7 | 0.5 | 2.5 | 69 |
| Lu 18-134 | 1.9 | 11.7 | 57 | 4.9 | <5 | |
| Lu 18-157 | 5.0 | | | | | 68 |
| Lu 18-159 | 15 | | | | | 40 |
| Lu 18-162 | 29 | | | | | |
| Lu 18-182 | 0.2 | 0.2 | 0.2 | | | 56 |
| Lu 18-185 | 0.2 | 0.3 | 0.3 | | | |
| chlorpromazine | 5.6 | 21 | 25 | 1.19 | 5 | 56.5 |
| fluphenazine | 0.04 | 0.7 | 0.3 | 0.43 | 2.5–5 | 98 |
| haloperidol | 0.04 | 0.4 | 0.4 | 1.0 | <~5 | 226 ip |
| morfine | >40 | | | | 2.5 | >320 |
| codeine | >20 | | | | 20 | 110 |
| dextropropoxyphene | >20 | | | | 20 | 34 |

Some of the novel indanes of Formula I have effects as dopamine uptake inhibitors at the same level as the known antidepressant nomifensine, and such effects have been associated with antidepressant effect.

The results obtained will appear from the following table:

TABLE 9

| Code Number | $^3$H-DA uptake, IC$_{50}$ (nM) |
|---|---|
| Lu 14-036 | 73 |
| Lu 14-048 | 46 |
| Lu 14-067 | 68 |
| Lu 14-068 | 84 |
| Lu 17-030 | 44 |
| Lu 17-066 | 27 |
| Lu 17-079 | 12 |
| Lu 17-109 | 4 |
| Lu 17-110 | 11 |
| Lu 17-132 | 12 |

TABLE 9-continued

| Code Number | $^3$H-DA uptake, IC$_{50}$ (nM) |
|---|---|
| Lu 17-133 | 3 |
| Lu 17-144 | 18 |
| Lu 17-152 | 88 |
| Lu 18-080 | 25 |
| Lu 18-081 | 15 |
| Lu 18-082 | 6 |
| Lu 18-120 | 5 |
| Lu 18-121 | 11 |
| Lu 18-128 | 12 |
| Lu 18-129 | 14 |
| Nomifensine | 50 |

The compounds of Formula I and the non-toxic acid addition salts thereof may be administered to animals such as dogs, cats, horses, sheeps or the like, including human beings, both orally and parenterally, and may be used for example in the form of tablets, capsules, powders, syrups or in the form of the usual sterile solutions for injection.

Results upon administration to human beings have been very gratifying.

Most conveniently the compounds of Formula I are administered orally in unit dosage form such as tablets or capsules, each dosage unit containing a non-toxic acid addition salt of one of the said compounds in an amount of from about 0.10 to about 100 mg, most preferably, however, from about 5 to 50 mg, calculated as the free amine, the total daily dosage usually ranging from about 1.0 to about 500 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

When the compound of Formula I is an ester, perferably a decanoic acid ester, palmitic acid ester or a behenic acid ester, the composition may advantageously be an oily solution for injection, and such solutions often have a very prolonged effect when compared with the corresponding unesterified compound.

Typical examples of formulas for composition containing 1-(2-hydroxyethyl)-4-(3-(4'-fluorophenyl)-6-fluoro-1-indanyl)piperazine (called Lu 13-117 for short) as the active ingredient, are as follows:

(1) Tablets containing 5 milligrams of Lu 13-117 calculated as the free base:

| | |
|---|---|
| Lu 13-117 | 5 mg |
| Lactose | 18 mg |
| Potato starch | 27 mg |
| Saccharose | 58 mg |
| Sorbitol | 3 mg |
| Talcum | 5 mg |
| Gelatine | 2 mg |
| Povidone | 1 mg |
| Magnesium stearate | 0.5 mg |

(2) Tablets containing 50 milligrams of Lu 13-117 calculated as the free base:

| | |
|---|---|
| Lu 13-117 | 50 mg |
| Lactose | 16 mg |
| Potato starch | 45 mg |
| Saccharose | 106 mg |
| Sorbitol | 6 mg |
| Talcum | 9 mg |
| Gelatine | 4 mg |
| Povidone | 3 mg |
| Magnesium stearate | 0.6 mg |

(3) Syrup containing per milliliter:

| | |
|---|---|
| Lu 13-117 | 10 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |

(4) Solution for injection containing per milliliter:

| | |
|---|---|
| Lu 13-117 | 50 mg |
| Acetic acid | 17.9 mg |
| Sterile water | ad 1 ml |

(5) Solution for injection containing per milliliter:

| | |
|---|---|
| Lu 13-117 | 10 mg |
| Sorbitol | 42.9 mg |
| Acetic acid | 0.63 mg |
| Sodium hydroxide | 22 mg |
| Sterile water | ad 1 ml |

Any other pharmaceutical tableting adjuvants may be used provided that they are compatible with the active ingredient, and additional compositions and dosage forms may be similar to those presently used for neuroleptics, such as thiothixene, clopenthixol or flupenthixol.

Also combinations of the compounds of Formula I as well as their non-toxic acid salts with other active ingredients, especially other neuroleptics, thymoleptics, tranquilizers, analgetics or the like, fall within the scope of the present invention.

As previously stated, when isolating the compounds of Formula I in the form of an acid addition salt the acid is preferably selected so as to contain an anion which is non-toxic and pharmacologically acceptable, at least in usual therepeutic doses. Representative salts which are included in this preferred group are the hydrochlorides, hydrobromides, sulphates, acetates, phosphates, nitrates, methanesulphonates, ethane-sulphonates, lactates, citrates, tartrates or bitartrates, embonates and maleates of the amines of Formula I. Other acids are likewise suitable and may be employed if desired. For example; fumaric, benzoic, ascorbic, succinic, salicylic, bismethylenesalicylic, propionic, gluconic, malic, malonic, mandelic, cannamic, citraconic, stearic, palmitic, itaconic, glycolic, benzenesulphonic, and sulphamic acids may also be employed as acid addition saltforming acids.

When it is desired to isolate a compound of the invention in the form of the free base, this may be done according to conventional procedure as by dissolving the isolated or unisolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalies of animals, including psychoses, depressions, pains or the like, by administering to a living animal body, including human beings, an adequate quantity of a compound of Formula I or a non-toxic acid addition salt thereof. An adequate quantity would be from about 0.001 mg to about 10 mg per kg of body weight in each unit dosage, and from about 0.003 milligrams to about 7 milligrams/kg of body weight per day.

It is to be understood that the invention is not limited to the exact details of operation or exact compound or compositions shown and described, as obvious modifications and equivalents will be apparent to one skilled in the art.

I claim:

1. A compound selected from the group consisting of a 1-piperazino-3-phenylindane of the formula:

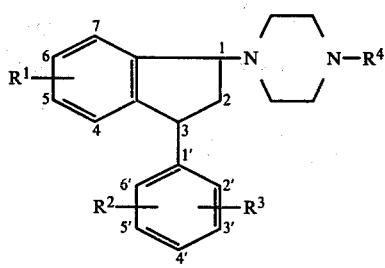

wherein $R^1$ is selected from the group consisting of hydrogen, halogen, an alkyl group having one to four carbon atoms inclusive, an alkyloxy group having one to four carbon atoms inclusive, an alkylmercapto group having one to four carbon atoms inclusive, an amino group, an acetamino group, a cyano group, a trifluoromethyl group and an alkylsulfonyl group having one to four carbon atoms inclusive; $R^2$ and $R^3$ are each selected from hydrogen, halogen, alkyl and trifluoromethyl; and $R^4$ is selected from an alkyl and alkenyl group, branched or unbranched, having one to six carbon atoms inclusive optionally substituted with one or two hydroxyl groups, a cyano group, an acetamino group, a cycloalkyl group having three to six carbon atoms in the ring, a phenyl group optionally substituted with a halogen atom, a hydroxy-substituted cyclohexyl group, a group

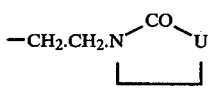

wherein U is $>O$ or $>NH$, and a group $—(CH_2)_n—CO.phenyl$ wherein "n" is an integer of one to four inclusive, and the phenyl group may be optionally substituted with a halogen atom, any hydroxy group present in the indane of Formula I being optionally esterified with an aliphatic carboxylic acid having two to twenty-four carbon atoms inclusive, at least one of both $R^1$, $R^2$ or $R^2$, $R^3$ always being other than hydrogen, and (2) a pharmaceutically-acceptable acid addition salt thereof.

2. A compound according to claim 1, wherein $R^1$ is selected from fluorine, $CF_3$, chlorine, methyl and methylmercapto in the 6-position; $R^2$ is fluorine in the 4'-position; $R^3$ is hydrogen, and $R^4$ is selected from methyl, 2-hydroxyethyl, 2,3-dihydroxy propyl, 3-hydroxy-propyl 4-hydroxybutyl, 1,3-dihydroxy-2-propyl and β-hydroxy propyl, or a pharmaceutically acceptable acid addition salt thereof.

3. A compound according to claim 1, selected from (1) the following named compounds:
   1-(2-hydroxyethyl)-4-(3-(4'-fluorophenyl)-6-trifluoromethyl-1-indanyl)piperazine
   1-(2-hydroxyethyl)-4-(3-(4'-fluorophenyl)-6-fluoro-1-indanyl)piperazine
   1-(4-hydroxybutyl)-4-(3-(4'-fluorophenyl)-6-fluoro-1-indanyl)piperazine
   1-isopropyl-4-(3-(4'-fluorophenyl)-6-methyl-1-indanyl)piperazine
   1-(3-hydroxypropyl)-4-(3-(4'-fluorophenyl)-6-chloro-1-indanyl)piperazine,
   and (2) isomers of one of said compounds; and (3) a pharmaceutically acceptable acid addition salt thereof.

4. A compound according to claim 1, wherein $R^1$ is hydrogen; $R^2$ is chlorine in the 3'-position; $R^3$ is chlorine in the 4'-position, and $R^4$ is selected from methyl, 2-hydroxyethyl, 2,3-dihydroxypropyl, 3-hydroxypropyl, 4-hydroxybutyl, 1,3-dihydroxy-2-propyl, isopropyl and β-hydroxypropyl, or a pharmaceutically acceptable salt thereof.

5. A compound according to claim 1, selected from (1) the following named compounds:
   1-(2-hydroxyethyl)-4-(3-(3',4'-dichlorophenyl)-1-indanyl)piperazine
   1-methyl-4-(3-(3',4'-dichlorophenyl)-1-indanyl)piperazine, and (2) an isomer of one of said compounds; and (3) a pharmaceutically acceptable acid addition salt thereof.

6. A pharmaceutical composition suitable for treating neuroleptic or depressant disorders in unit dosage form comprising—as active ingredient—an effective neuroleptic or antidepressant amount of a compound as defined in claim 1, and one or more pharmaceutical diluents or carriers.

7. A pharmaceutical composition in unit dosage form, according to claim 6, —wherein the active ingredient is present in an amount from 0.10 to 100 milligrams per unit dosage.

8. A method for the treatment of psychic disorders in warm-blooded animals, including human beings, which comprises administering an effective neuroleptic or antidepressant quantity of a compound of Formula I, as defined in claim 1.

9. A method according to claim 8, which comprises, administering the compound as a pharmaceutical composition in unit dosage form in a quantity of from 0.001 mg to 10 mg per kg body weight.

10. A compound of the formula I in claim 1 wherein $R^1$ is 6-methyl, $R^2$ is 4'-fluoro, $R^3$ is hydrogen, and $R^4$ is an alkyl or hydroxyalkyl group having from 1 to 6 carbon atoms, or a pharmaceutically acceptable acid addition salt thereof.

11. A compound of formula I in claim 1 wherein the compound is 1-methyl-4-(3-(4'-fluorophenyl)-6-fluoro-1-indanyl)piperazine, or a pharmaceutically acceptable acid salt thereof.

12. A compound of formula I in claim 1 wherein $R^1$ is halogen, $R^2$ is halogen, $R^3$ is hydrogen, and $R^4$ is an alkyl group having from 1 to 6 carbon atoms, or a pharmaceutically acceptable acid addition salt thereof.

13. The compound of formula I in claim 1 which is 1-isopropyl(3-(4'-fluorophenyl)-6-fluoro-1-indanyl)piperazine, or a pharmaceutically acceptable acid addition salt thereof.

14. The compound of formula I in claim 1 wherein the compound is 1-(2-hydroxypropyl)-4-(3-(4'-fluorophenyl)-6-fluoro-1-indanyl)piperazine, or a pharmaceutically acceptable acid addition salt thereof.

15. The compound of formula I in claim 1 wherein the compound is 1-(3-phenyl-2-propenyl)-4-(3-(4'-fluorophenyl)-6-fluoro-1-indanyl)piperazine, or a pharmaceutically acceptable acid addition salt thereof.

16. The compound of formula I in claim 1 wherein the compound is 1-cyclopropylmethyl-4-(3-(4'-fluorophenyl)-6-fluoro-1-indanyl)piperazine, or a pharmaceutically acceptable acid addition salt thereof.

17. The compound of formula 1 in claim 1 wherein the compound is cis-1-methyl-4-(3-(4'-fluorophenyl)-6-fluoro-1-indanyl)piperazine, or a pharmaceutically acceptable salt thereof.

18. The compound of formula 1 in claim 1 wherein the compound is 1-(1,3-dihydroxypropyl)-4-(3-(4'-fluorophenyl)-6-fluoro-1-indanyl)piperazine, or a pharmaceutically acceptable acid addition salt thereof.

19. The compound of formula 1 in claim 1 wherein the compound is the decanoic acid ester of 1-(2-hydroxyethyl)-4-(3-(4'-fluorophenyl)-6-fluoro-1-indanyl)piperazine, or a pharmaceutically acceptable acid addition salt thereof.

20. The compound of formula 1 in claim 1 wherein the compound is the (+) isomer of 1-methyl-4-(3-(4'-fluorophenyl)-6-fluoro-1-indanyl)piperazine, or a pharmaceutically acceptable acid addition salt thereof.

21. The compound of formula 1 in claim 1 wherein the compound is the (−) isomer of 1-methyl-4-(3-(4'-fluorophenyl)-6-fluoro-1-indanyl)piperazine, or a pharmaceutically acceptable salt thereof.

22. A compound of claim 1, which is selected from the group consisting of 1-(2-hydroxyethyl)-4-(3-(4'-fluorophenyl)-6-fluoro-1-indanyl)piperazine decanoate, palmitate, or behenate, and a pharmaceutically-acceptable acid addition salt thereof.

23. A compound of claim 1, which is selected from the group consisting of 1-(2-hydroxyethyl)-4-(3-(4'-fluorophenyl)-6-trifluoromethyl-1-indanyl)piperazine, valerate, or decanoate and a pharmaceutically-acceptable acid addition salt thereof.

24. A compound of claim 1, which is selected from the group consisting of 1-(hydroxy-loweralkyl)-4-(3-(4'-fluorophenyl)-6-Q-1-indanyl)piperazine and a pharmaceutically-acceptable acid addition salt thereof, wherein Q is trifluoromethyl, fluoro, or chloro.

25. A compound of claim 1, which is selected from the group consisting of 1-(hydroxy-loweralkyl)-4-(3-(3',4'-dichlorophenyl)-1-indanyl)piperazine and a pharmaceutically-acceptable acid addition salt thereof.

26. A compound of claim 1, which is selected from the group consisting of 1-(2-hydroxyethyl)-4-(3-(4'-fluorophenyl)-6-trifluoromethyl-1-indanyl)piperazine, and a pharmaceutically-acceptable acid addition salt thereof.

27. A compound of claim 1, which is selected from the group consisting of 1-(2-hydroxyethyl)-4-(3-(4'-fluorophenyl)-6-fluoro-1-indanyl)piperazine, and a pharmaceutically-acceptable acid addition salt thereof.

28. A compound of claim 1, which is selected from the group consisting of 1-(4-hydroxybutyl)-4-(3-(4'-fluorophenyl)-6-fluoro-1-indanyl)piperazine, and a pharmaceutically-acceptable acid addition salt thereof.

29. A compound of claim 1, which is selected from the group consisting of 1-isopropyl-4-(3-(4'-fluorophenyl)-6-methyl-1-indanyl)piperazine, and a pharmaceutically-acceptable acid addition salt thereof.

30. A compound of claim 1, which is selected from the group consisting of 1-(3-hydroxypropyl)-4-(3-(4'-fluorophenyl)-6-chloro-1-indanyl)piperazine, and a pharmaceutically-acceptable acid addition salt thereof.

31. A compound of claim 1, which is selected from the group consisting of 1-(2-hydroxyethyl)-4-(3-(3',4'-dichlorophenyl)-1-indanyl)piperazine, and a pharmaceutically-acceptable acid addition salt thereof.

32. A compound of claim 1, which is selected from the group consisting of 1-methyl-4-(3-(3',4'-dichlorophenyl)-1-indanyl)piperazine, and a pharmaceutically-acceptable acid addition salt thereof.

* * * * *

UNITED STATES PATENT AND TRADEMARK OFFICE
CERTIFICATE OF CORRECTION

PATENT NO. : 4,443,448

DATED : April 17, 1984

INVENTOR(S) : Klaus P. Bøgesø

It is certified that error appears in the above—identified patent and that said Letters Patent is hereby corrected as shown below:

Col. 2, line 4; "-fuoro-" should read -- -fluoro- --
Col. 3, line 42; after "are" insert -- as --
Col. 4, line 64; "compounds" should read -- compound --
Col. 5, line 28; after "lithium" insert -- aluminium --
Col. 8, approximately line 30, in the formula under "Method A", change "$CH_3$" to -- $CH_2$ --
Col. 9, line 28; delete "be" (first occurrence)
Col. 11, Table 2, Col. 4, line 17; "122-123" should read -- 121-123 --
Col. 13, line 25; "to" should read -- in --
Col. 13, line 66; "tolune," should read -- toluene, --
Col. 15, line 9; after "of" insert -- a --
Cols. 15 & 16, Table 5, last column, line 42; "dichloride" should read -- dihydrochloride --
Col. 23, line 20; "-indanyl-" should read -- -indanyl)- --
Col. 23, line 68; "drived" should read -- dried --
Col. 24, lines 50 & 51; change "," after "dihydrochlorides" to -- . --
Col. 24, line 52; "propy)-" should read -- propyl)- --
Col. 25, line 17; "decaonate," should read -- decanoate, --
Col. 26, line 16; "were" should read -- are --
Col. 33, line 2; insert at beginning of the line; -- (1) --

Col. 33, line 46; delete "at least one of".

UNITED STATES PATENT AND TRADEMARK OFFICE
CERTIFICATE OF CORRECTION

PATENT NO. : 4,443,448

DATED : April 17, 1984

INVENTOR(S) : Klaus P. Bøgesø

It is certified that error appears in the above—identified patent and that said Letters Patent is hereby corrected as shown below:

Col. 9, line 11; "clousure" should read -- closure --
Col. 16, line 9; "cromatography." should read -- chromatography. --
Col. 16, line 17; "neurcleptic" should read -- neuroleptic --
Cols. 15 & 16, Table 5, column 1, lines 22 through 41; insert -- Lu -- before the numbers in each instance
Cols. 15 & 16, Table 5, column 3, lines 14 and 16; change "3'-CL" to -- 3'-Cl -- in both instances
Cols. 17 & 18, Table 5-continued, column 1, lines 6 through the end of the Table; insert -- Lu -- before the numbers in each instance
Col. 23, line 22; "ans" should read -- and --
Col. 27, line 6; "nor" should read -- not --
Col. 32, lines 65 & 66; "medifications" should read -- modifications --

Signed and Sealed this

Ninth Day of April 1985

[SEAL]

Attest:

DONALD J. QUIGG

*Attesting Officer*   *Acting Commissioner of Patents and Trademarks*